United States Patent
Cheng et al.

(10) Patent No.: US 6,967,096 B2
(45) Date of Patent: Nov. 22, 2005

(54) THERMOSTABLE PEPTIDASE

(75) Inventors: Timothy C. Cheng, Pasadena, CA (US); Vij Ramakrishnan, Pasadena, CA (US); Sunney I. Chan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 430 days.

(21) Appl. No.: 09/969,125

(22) Filed: Sep. 24, 2001

(65) Prior Publication Data

US 2002/0106779 A1 Aug. 8, 2002

Related U.S. Application Data

(62) Division of application No. 09/333,768, filed on Jun. 15, 1999, now Pat. No. 6,294,367.
(60) Provisional application No. 60/089,398, filed on Jun. 15, 1998.

(51) Int. Cl.[7] ............................. C12N 9/48; C07K 1/00

(52) U.S. Cl. ...................................... 435/212; 530/350

(58) Field of Search .......................... 435/212; 530/350

(56) References Cited

PUBLICATIONS

Ishikawa et al., Faseb J., Jul. 1997, 11(9), A1013.*
Davison et al., Virology, 186, 9–14.
Lee et al., Biotech Biochem., 58(8), 1490–1495.

* cited by examiner

*Primary Examiner*—Maryam Monshipouri
(74) *Attorney, Agent, or Firm*—Fish & Richardson P.C.

(57) ABSTRACT

Thermostable peptidase enzyme derived from archaeon from the genus *Pyrococcus* is disclosed. The enzyme is produced from native or recombinant host cells and can be utilized in the biotechnology industry as a useful enzyme in sequencing reactions.

8 Claims, 12 Drawing Sheets

```
Pfu-N   ............MEEVFQNETIKQILAKYRRIWAIGHAQRVL         - SEQ ID NO:1
            ||||:|::|||.:|||||||||||:|||.||
Pho   1 METVLRRLHLEKSGETMEEVFRNDTIKEILQKYRRIWALGHAQSVL 46

Pfu-I    EGILERSVAQGELSVLSHELLLHPEFVNLVEK              - SEQ ID NO:2
         |||||||||||||||:|:|||:|||||.|||
Pho  57  EGILERSVAQGELSVLSQELLLKPEFVELVEK 88

Pfu-II   AIGEDMDAEYFVRWVK                              - SEQ ID NO:3
         ||||||:::|||||:|
Pho  496 AIGEDVNAEYFVRWIK 511
```

FIG. 3

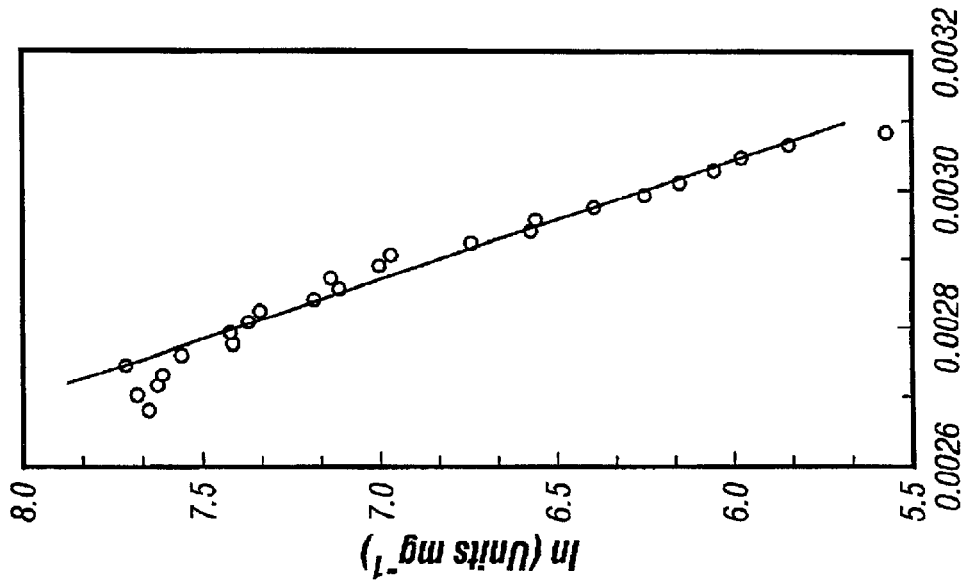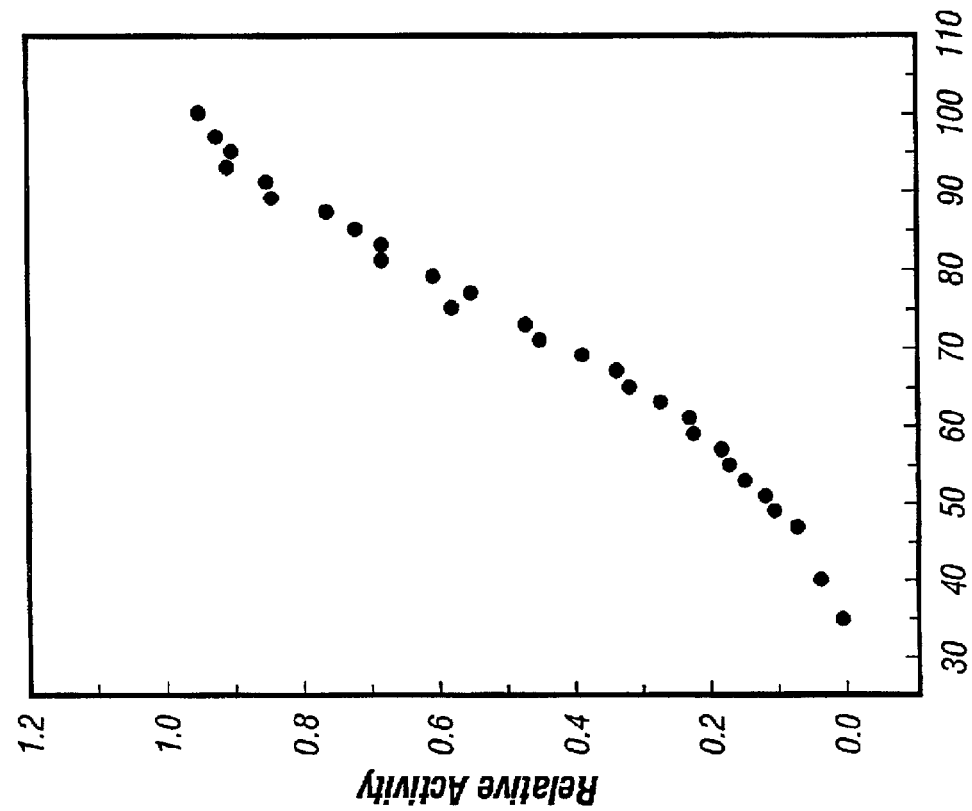

Table I
Purification of PfuCP from P. furiosus

| Purification Step | Total Protein (mg) | Units (U.ml$^{-1}$) | Specific Activity (U.mg$^{-1}$) | Purification Fold | Yield (%) |
|---|---|---|---|---|---|
| Crude extract | 21404 | 171250 | 8 | 1 | 100 |
| Q FastFlow | 2398 | 110862 | 46 | 6 | 65 |
| Hydroxyapatite | 750 | 99696 | 133 | 17 | 58 |
| Butyl Sepharose | 183 | 82765 | 452 | 57 | 48 |
| Q High Performance | 14 | 15831 | 1131 | 141 | 9.2 |
| Superdex | 13 | 16941 | 1303 | 163 | 9.9 |
| Mono-Q | 11 | 15306 | 1391 | 174 | 8.9 |

FIG. 12

THERMOSTABLE PEPTIDASE

CROSS REFERENCE TO RELATED APPLICATIONS

This application is a divisional application of Ser. No. 09/333,768, filed Jun. 15, 1999 (now U.S. Pat. No. 6,294,367), which claims priority from Provisional Application Ser. No. 60/089,398, filed Jun. 15, 1998, which is incorporated by reference in its entirety and to which application is a priority claim is made under 35 U.S.C. §119(e).

The U.S. Government has certain rights in this invention pursuant to Grant No. GM 22432-23 awarded by the National Institute of Health.

FIELD OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been identified as a thermostable peptidase.

BACKGROUND OF THE INVENTION

Hyperthermophiles are microorganisms which grow optimally at temperatures of 80° C. and above (Huber et al., *J. Biotechnol.* 64, 39–52 (1998)). A majority of these organisms fall under the newly identified domain, archaea (Woese et al., *Proc. Nat. Acad. Sci USA* 87, 4576–4579 (1990)). One of the most extensively studied hyperthermophilic archaea is *Pyrococcus furiosus* (Pfu). This microorganism has a growth optimum of 100° C. (Fiala et al., *Arch. Microbiol.* 145, 56–61 (1986)). It is a heterotrophic, anaerobic archaeon, and utilizes complex carbohydrates and peptides/proteins as carbon and energy sources (Adams et al., *Adv. Protein Chem.* 48, 101–180 (1996)). The metabolic end products are organic acids, alanine, $CO_2$ and $H_2$ (Kengen et al., *Arch. Microbiol.* 161, 168–175 (1994); Kengen et al., *FEMS Microbiol. Rev.* 18, 119–137 (1996)). Additional energy is generated when excess redox equivalents are channeled to elemental sulfur (Schicho et al., *J. Bacteriol.* 175, 1823–1830 (1993)).

Most of the proteins isolated from these hyperthermophiles exhibit a temperature optimum of at least 80–100° C. or above (Adams et al., *Bio/Technology* 13, 662–668 (1995); Adams et al., *Trends Biotechnol* 16, 329–332 (1998)). Accordingly, there is much interest in exploiting these proteins for biotechnological applications, as they are able to perform biochemical reactions under harsh conditions, such as in the presence of high-temperatures, organic solvents, and denaturants (Adams et al., supra.) *P. furiosus* has been the source of many of these biotechnologically important proteins, including DNA polymerase (Lundberg et al., *Gene* 108, 1–6 (1991)), α-amylase (Laderman et al., *J. Biol. Chem.* 268, 24394–24401 (1993)), and proteases (Voorhorst et al., *J. Biol. Chem.* 271, 20426–20431 (1996); Harwood et al., *J. Bacteriol.* 179, 3613–3618 (1997)).

Peptidases hydrolyze peptide bonds from peptide and protein molecules, For example, carboxypeptidases sequentially hydrolyze peptide bonds from the C-terminus of proteins and polypeptides. They are ubiquitous in animals, plants and microorganisms; many carboxypeptidases have been characterized based on their substrate specificity and mechanism (serine- versus metallo-carboxypeptidase) (Skidgel et al., *Immunol. Rev.* 161, 129–141 (1998)). Carboxypeptidases have been implicated in physiological roles such as protein degradation/turnover, or processing of precursor proteins (Steiner, D. F., *Curr. Opin. Chem. Biol.* 2, 31–39 (1998)), and in the metabolism of proteins and peptides as carbon or energy sources. Most of the purified carboxypeptidases have a temperature optimum below 40° C. However, three moderately thermostable carboxypeptidases have been purified from the bacteria *Thermoactinomyces vulgaris* (Stepanov et al., *T. Methods Enzymol.* 248, 675–683 (1995)), and *Thermus aquaticus* (Lee et al., Biosci. Biotechnol. Biochem. 56, 1839–1844 (1992)), and the archaeon *Sulfolobus solfataricus* (Colombo et al., *Eur. J. Biochem.* 206, 349–357 (1992)), with temperature optima of 60, 80, and 85° C., respectively. Carboxypeptidase activity has not yet been reported for *P. furiosus*.

Protein sequencing is an integral component of modern biochemical research. Edman degradation is useful for N-terminal sequencing, but it fails when the amino terminus is chemically protected. Aside from endoproteolytic fragmentation, another way to obtain sequence information from proteins is to sequence from the C-terminus. Various C-terminal sequencing methods have been developed: chemical cleavage analogous to Edman degradation (Hardeman et al., *Protein Sci.* 7, 1593–1602 (1998)), and enzymatic digestion by carboxypeptidases (Thiede et al., *Eur. J. Biochem.* 244, 750–754 (1997)). A particularly powerful approach is enzymatic ladder sequencing, in which a carboxypeptidase is used to generate a set of differentially cleaved peptides that can be visualized in a mass spectrum; mass differences between adjacent peaks correspond to the molecular masses of individual amino acids that have been released. Enzymatic protein ladder sequencing has the potential to sequence as far as the enzyme can cut. However, a number of difficulties have limited the applicability of this approach: i) the limited specificities of a given carboxypeptidase toward the 20 common amino acids; and ii) the resistance of native protein molecules to digestion at mesophilic temperatures.

There is a need for novel peptidase enzymes having enhanced thermostability. This includes a need for thermostable C-terminal peptidases whose enhanced thermostability is beneficial in sequencing reactions.

SUMMARY OF THE INVENTION

In one aspect, the present invention provides compositions and methods useful in C-terminal sequencing of proteins and polypeptides. A hyperthermophilic carboxypeptidase of the present invention is catalytically active at temperatures where the tertiary structures of most mesophilic proteins are denatured. Accordingly, the use of the carboxypeptidase of the invention provides distinct advantages over previous peptidases used in sequencing of polypeptides. Additionally, the specificity of a thermophilic carboxypeptidase of the invention is broader than most of its mesophilic counterparts.

In one embodiment the present invention provides a substantially purified polypeptide characterized as a thermostable carboxypeptidase. The carboxypeptidase is a metallocarboxypeptidase and has a monomeric molecular weight of about 58 kDa by SDS-PAGE; a monomeric molecular weight of about 59 kDa as determined by matrix-assisted laser desorption ionization time-of-flight mass spectrometry; and a dimeric molecular weight of about 128 kDa by gel filtration chromatography. In another aspect of the invention the carboxypeptidase activity is dependent on the presence of the divalent cation (e.g., $Co^{2+}$, $Ca^{2+}$, $Ni^{2+}$, $Mn^{2+}$, $Fe^{2+}$, $Cd^{2+}$, $Cu^{2+}$, $Pb^{2+}$, $Rh^{2+}$). The purified carboxypeptidase can be obtained from the genus *Pyrococcus*. A preferred source is *P. furiosus*. In yet a further embodiment, the polypeptide of the invention has a sequence as set forth in SEQ ID Nos 1, 2, or 3.

In another embodiment the present invention provides a polynucleotide encoding a thermostable carboxypeptidase, as well as vectors containing the polynucleotide and host cells containing a vector with a polynucleotide encoding a thermostable carboxypeptidase.

In yet another embodiment, the present invention provides an anti-polypeptide antibody that binds to a thermostable carboxypeptidase of the invention. The antibody may be monoclonal or polyclonal.

In another embodiment, a process for producing a polypeptide characterized as a thermostable carboxypeptidase is provided. The process includes expressing from a host cell a thermostable carboxypeptidase polypeptide encoded by a polynucleotide of the invention.

Also provided is a process for producing a cell by transforming or transfecting the cell with a vector containing a polynucleotide encoding a thermostable carboxypeptidase such that the cell expresses the polypeptide encoded by the polynucleotide.

The present invention also provides a method for sequencing a polypeptide's amino acid sequence, comprising contacting a polypeptide with a thermostable carboxypeptidase having a temperature optimum exceeding 90° C., wherein the carboxypeptidase hydrolyzes peptide bonds in the polypeptide; and identifying the enzymatic products.

These and other aspects of the present invention will be apparent to those of skill in the art from the teachings herein.

BRIEF DESCRIPTION OF THE DRAWINGS

The following drawings are illustrative of embodiments of the invention and are not meant to limit the scope of the invention as encompassed by the claims.

FIG. 3 shows the amino acid sequence analysis of PfuCP. The amino acid sequences of the N-terminus (Pfu-N) and two Endo-Lys C fragments of PfuCP (Pfu-I and Pfu-II) were aligned with the sequence of the putative *P. horikoshii* carboxypeptidase (PhoCP) using the GAP program from GCG software v.8. The gap weight was 3.0 and the extension penalty was 0.1. The N-terminal extension of the PhoCP gene product is also shown.

FIG. 12 is a table showing the purification of PfuCP from *P. furiosus*.

DETAILED DESCRIPTION OF THE INVENTION

Figure 1:
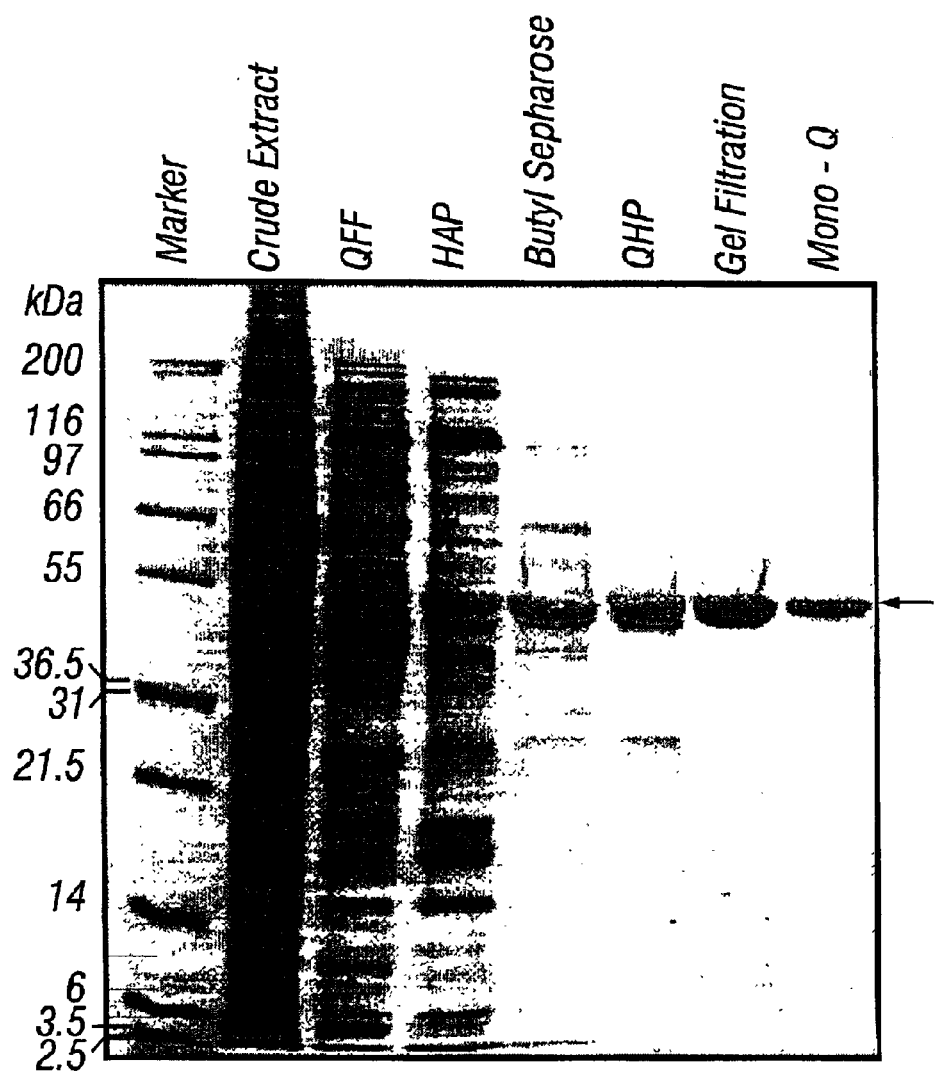
FIG. 1 shows the purification of PfuCP from *P. furiosus* crude extract. The fractions containing maximum activity from each purification step were analyzed by denaturing and reducing SDS-PAGE. Samples were pre-incubated at 80° C. for 1 min in 0.1% SDS and run on a 12% Tris-glycine gel.

Peptidases are a class of enzymes, which play an important role in the processing of proteins. The body uses this mechanism to control several critical pathways or biochemical cascades, such as blood clot formation and complement activation. In neurons, specific proteases control pathways critical to neuronal communication and survival. Abnormal neuronal protease activity can lead to degenerative processes, as occurs during progressive disorders such as Alzheimer's disease and in phases of acute neuronal cell death resulting from head trauma and ischemia due to stroke. For example, these proteases can generate products that are neurotoxic, such as the amyloid beta protein ("Aβ") which forms the senile plaques seen in Alzheimer's disease patients, or initiate degradative cascades that are involved in breaking down the neuronal cytoskeleton, leading to nerve cell death.

The term "protease" is synonymous with "peptidase". Proteases comprise two groups of enzymes: the endopeptidases which cleave peptide bonds at points within the protein, and the exopeptidases, which remove amino acids sequentially from either the N or C-terminus, respectively. The term proteinase is also used as a synonym for endopeptidase. The four mechanistic classes of proteases are: serine proteases, cysteine proteases, aspartic proteases, and metallo proteases. In addition to these four mechanistic classes, there is a section of the enzyme nomenclature which is allocated for proteases of unidentified catalytic mechanism. This indicates that the catalytic mechanism has not been identified. Thus, the possibility remains that novel types of proteases do exist.

The serine proteases include two distinct families. The chymotrypsin family which includes the mammalian enzymes such as chymotrypsin, trypsin, elastase, kallikrein and the subtilisin family which includes the bacterial enzymes such as subtilisin. The general 3D structure is different in the two families but they have the same active site geometry and catalysis proceeds via the same mechanism. The serine proteases exhibit different substrate specificities which are related to amino acid substitutions in the various enzyme subsites interacting with the substrate residues. Some enzymes have an extended interaction site with the substrate whereas others have a specificity restricted to the P1 substrate residue.

The cysteine proteases include plant proteases such as papain, actinidin or bromelain, several mammalian lysosomal cathepsins and, calcium-activated cytosolic calpains as well as several parasitic proteases (e.g *Trypanosoma, Schistosoma*). Papain is the archetype and the best studied member of the family. Recent elucidation of the X-ray structure of the Interleukin-1-beta Converting Enzyme has revealed a novel type of fold for cysteine proteinases. Like the serine proteases, catalysis proceeds through the formation of a covalent intermediate and involves a cysteine and a histidine residue.

Most of aspartic proteinases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteinases such as the protease from the AIDS virus (HIV), also called retropepsin. Crystallographic studies have shown that these enzymes are bi-lobed molecules with the active site located between two homologous lobes. Each lobe contributes one aspartate residue of the catalytically active diad of aspartates.

The metallo proteinases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain a specific sequence which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a noncovalent tetrahedral intermediate after the attack of a zinc-bound water molecule on the carbonyl group of the scissile bond. This intermediate is further decomposed by transfer of the glutamic acid proton to the leaving group.

The present invention provides polypeptides and polynucleotides encoding the polypeptides, wherein the polypeptide is characterized as a thermostable peptidase. To facilitate understanding of the invention, a number of terms are defined below.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the nucleic acid and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions), and therein remain isolated polynucleotides or polypeptides within the meaning of that term as it is employed herein.

The term "ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989).

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., Meth. Enzymol., 68, 90–99, (1979); the phosphodiester method of Brown et al., Method. Enzymol. 68, 109–151, (1979); the diethylphosphoramidite method of Beaucage et al., Tetrahedron Lett., 22, 1859–1862, (1981); the triester method of Matteucci et al., J. Am. Chem. Soc., 103, 3185–3191, (1981); or automated synthesis methods; and the solid support method of U.S. Pat. No. 4,458,066.

The term "plasmids" generally is designated herein by a lower case p preceded and/or followed by capital letters and/or numbers, in accordance with standard naming conventions that are familiar to those of skill in the art.

Plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide" or "nucleic acid sequence" refers to a polymeric form of nucleotides at least 10 bases in length. By "isolated nucleic acid sequence" is meant a polynucleotide that is not immediately contiguous with both of the coding sequence with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

Nucleic acid sequences which encode a fusion protein of the invention can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the nucleic acid sequences encoding a fusion protein of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988), baculovirus-derived vectors for expression in insect cells, cauliflower mosaic virus, CaMV; tobacco mosaic virus, TMV. The nucleic acid sequences encoding a fusion polypeptide of the invention can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involves the use of molecular cloning techniques also well known in the art. Sambrook et al., *Molecular Cloning—A Laboratory Manual,* Cold Spring Harbor Laboratory, Cold Spring Harbor, N.Y., 1989, and *Current Protocols in Molecular Biology*, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., *Methods in Enzymology* 153:516–544, 1987). These elements are well known to one of skill in the art.

In yeast, a number of vectors containing constitutive or inducible promoters may be used. For a review see, *Current Protocols in Molecular Biology*, Vol. 2, Ed. Ausubel, et al., Greene Publish. Assoc. & Wiley Interscience, Ch. 13, 1988; Grant, et al., "Expression and Secretion Vectors for Yeast," in *Methods in Enzymology*, Eds. Wu & Grossman, 1987, Acad. Press, N.Y., Vol. 153, pp.516–544, 1987; Glover, *DNA Cloning*, Vol. II, IRL Press, Wash., D.C., Ch. 3, 1986; and Bitter, "Heterologous Gene Expression in Yeast," *Methods in Enzymology*, Eds. Berger & Kimmel, Acad. Press, N.Y., Vol. 152, pp. 673–684, 1987; and *The Molecular Biology of the Yeast Saccharomyces*, Eds. Strathern et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: *DNA Cloning Vol. 11, A Practical Approach*, Ed. DM Glover, IRL Press, Wash., D.C., 1986). Alternatively, vectors may be used which promote integration of foreign DNA sequences into the yeast chromosome.

An alternative expression system which could be used to express the proteins of the invention is an insect system. In one such system, *Autographa californica* nuclear polyhedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., a thermostable peptidase), or fragment thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell, including a human cell.

Eukaryotic systems, and mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the nucleic acid sequences encoding a fusion protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the thermostable peptidase in infected hosts (e.g., see Logan & Shenk, *Proc. Natl. Acad. Sci. USA*, 81:3655–3659, 1984). Alternatively, the vaccinia virus 7.5K promoter may be used. (e.g., see, Mackett, et al., *Proc. Natl. Acad. Sci. USA*, 79:7415–7419, 1982; Mackett, et al., *J. Virol.* 49:857–864, 1984; Panicali, et al., *Proc. Natl. Acad. Sci. USA* 79:4927–4931, 1982). of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the thermostable peptidase gene in host cells (Cone & Mulligan, *Proc. Natl. Acad. Sci. USA*, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA*, 77:3567, 1980; O'Hare, et al., *Proc. Natl. Acad. Sci. USA*, 8:1527, 1981); gpt, which confers resistance to mycophenolic acid (Mulligan & Berg, *Proc. Natl. Acad. Sci. USA*, 78:2072, 1981; neo, which confers resistance to the aminoglycoside G-418 (Colberre-Garapin, et al., *J. Mol. Biol.* 150:1, 1981); and hygro, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature.

The term "primer" may refer to more than one primer, particularly in the case where there is some ambiguity in the information regarding one or both ends of the target region to be synthesized. For instance, if a nucleic acid sequence is inferred from a protein sequence, a "primer" generated to synthesize nucleic acid encoding said protein sequence is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences. For example, primers can be synthesized based upon the amino acid sequence as set forth in SEQ ID No's 1, 2 or 3 and can be designed based upon the degeneracy of the genetic code.

The term "restriction endonucleases" and "restriction enzymes" refers to bacterial enzymes which cut double-stranded DNA at or near a specific nucleotide sequence.

The term "gene" means the segment of DNA involved in producing a polypeptide chain; it includes regions preceding and following the coding region (leader and trailer) as well as intervening sequences (introns) between individual coding segments (exons).

A coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme (e.g. the thermostable peptidase of the present invention). "Synthetic" enzymes are those prepared by chemical synthesis.

As used in connection with the present invention the term "polypeptide" or "protein" refers to a polymer in which the monomers are amino acid residues which are joined together through amide bonds. When the amino acids are alpha-amino acids, either the L-optical isomer or the D-optical isomer can be used, the L-isomers being preferred. The term "polypeptide" as used herein is intended to encompass any amino acid sequence and include modified sequences such as glycoproteins. The term "polypeptide" is specifically intended to cover naturally occurring proteins, as well as those which are recombinantly or synthetically synthesized, which occur in at least two different conformations wherein both conformations have the same or substantially the same amino acid sequence but have different three dimensional structures. "Fragments" are a portion of a naturally occurring protein. Fragments can have the same or substantially the same amino acid sequence as the naturally occurring protein. "Substantially the same" means that an amino acid sequence is largely, but not entirely, the same, but retains a functional activity of the sequence to which it is related. In general two amino acid sequences are substantially the same" or "substantially homologous" if they are at least 85% identical. The term "conservative variatio" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immuno-react with the unsubstituted polypeptide.

A DNA "coding sequence of" or a "nucleotide sequence encoding" a particular enzyme, is a DNA sequence which is transcribed and translated into an enzyme when placed under the control of appropriate regulatory sequences.

The term "thermostable peptidase" refers to an enzyme which is stable to heat, is heat-resistant, and catalyzes the removal of amino acids or peptide groups from a polypeptide or peptide sequence. Reference to "thermostable peptidase" includes carboxypeptidase.

A peptidase enzyme of the present invention cannot become irreversibly denatured (inactivated) when subjected to the elevated temperatures for the time necessary to effect the a removal or hydrolysis of an amino acid from a polypeptide sequence. Irreversible denaturation for purposes herein refers to permanent and complete loss of enzymatic activity. The peptidase enzymes of the invention do not become irreversibly denatured from exposure to temperatures of a range from about 60° C. to about 113° C. or more. The extreme thermostability of the peptidase enzyme provides additional advantages over previously characterized thermostable enzymes. Prior to the present invention, efficient digestion of peptides at temperatures as high as 100° C. has not been demonstrated.

In accordance with one aspect of the present invention, there are provided isolated polypeptides characterized as thermostable carboxypeptidases, or functional fragments thereof.

The polypeptides of the invention were originally recovered from the hyperthermophilic archaeon, *Pyrococcus furiosus*. The polypeptide of the present invention (e.g., a metallocarboxypeptidase (PfuCP)) was purified in its inactive state by the addition of ethylenediaminetetraacetic acid (EDTA) and dithiothreitol (DTT). The activity was restored by the addition of divalent cobalt ($K_d$=13±3 $\mu$m at 80° C.). Phenymethylsulfonyl fluoride (PMSF) had no effect on the enzymatic activity of the polypeptide. The molecular mass of monomeric PfuCP is 59 kDa as determined by matrix-assisted laser desorption ionization time-of-flight mass spectrometry (MALDI-TOF MS), and a relative mobility shift related to a mass of about 58 kDa by SDS-PAGE analysis. In solution, PfuCP exists as a homodimer of about 128 kDa as determined by gel filtration chromatography.

The activity of PfuCP exhibits a temperature optimum exceeding 90° C. under ambient pressure, and a pH optimum of 6.2–6.6. Addition of $Co^{2+}$ to the apoPfuCP at room temperature does not alter its far-UV circular dichroism or its intrinsic fluorescence spectrum. Even when the CoPfuCP is heated to 80° C., its far-UV circular dichroism shows a minimal change in the global conformation and the intrinsic fluorescence of aromatic residues shows only a partial quenching. Changes in the intrinsic fluorescence appear essentially reversible with temperature. Finally, the far-UV and intrinsic fluorescence data suggest that the overall structure of the holoenzyme is extremely thermostable. However, the activities of both the apo and holo enzyme exhibit a similar second-order decay over time, with 50% activity remaining after about 40 minutes at 80° C. The N-blocked synthetic dipeptide, N-Carbobenzoxy-Ala-Arg (ZAR), was used in the purification assay. The kinetic parameters at 80° C. with 0.4 mM $CoCl_2$ were: $K_m$, 2 mM; $V_{max}$, 2100 Units $mg^{-1}$; and turn over number, 2000 $sec^{-1}$. Activity against other ZAX substrates (X=V, L, I, M, W, Y, F, N, A, S, H, K) revealed a broad specificity for neutral, aromatic, polar and basic C-terminal residues.

The present invention further relates to thermostable peptidase enzymes which contain the amino acid sequence as set forth in SEQ ID No: 1, 2, or 3, as well as fragments, analogs and derivatives of such enzyme.

The terms "fragment", "derivative", and "analog" when referring to the polypeptide and enzyme of the present invention means enzymes which retain essentially the same biological function or activity as such enzymes. Such biological activity includes, for example, the ability to hydrolyze peptide bonds and antigenicity. Thus, an analog includes a proprotein which can be activated by cleavage of the proprotein portion to produce an active mature enzyme.

The enzymes of the present invention may be a recombinant enzyme, a natural enzyme or a synthetic enzyme, preferably a recombinant enzyme.

The fragment, derivative or analog of the polypeptide containing the sequences of SEQ ID No: 1, 2, or 3, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes, polypeptides and polynucleotides of the present invention are preferably provided in an isolated form, and preferably are purified to homogeneity.

The enzymes of the present invention include the polypeptide containing SEQ ID No's 1, 2, or 3, as well as enzymes which have at least 70% similarity (preferably at least 70% identity) to the polypeptides containing SEQ ID No.: 1, 2, or 3, and more preferably at least 90% similarity (more preferably at least 90% identity) and still more preferably at least 95% similarity (still more preferably at least 95% identity) to the enzymes and polypeptides of the present invention.

As known in the art "similarity" between two enzymes or polypeptides is determined by comparing the amino acid sequence and its conserved amino acid substitutes of one enzyme or polypeptide to the sequence of a second enzyme or polypeptide. The definition of 70% similarity would include a 70 amino acid sequence fragment of a 100 amino acid sequence, for example, or a 70 amino acid sequence obtained by sequentially or randomly deleting 30 amino acids from the 100 amino acid sequence.

A variant, i.e. a "fragment", "analog", or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

In accordance with an aspect of the present invention, there are provided isolated nucleic acids (polynucleotides) which encode for the mature enzymes or polypeptides having the amino acid sequences of FIG. 3 (SEQ ID NO: 1, 2, or 3).

The polynucleotides of this invention were originally recovered from the hyperthermophilic archaeon, *Pyrococcus furiosus*.

One means for isolating the nucleic acid molecules encoding the enzymes and polypeptides of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that probes can be designed based on the degeneracy of the genetic code to the sequences set forth in SEQ ID No's: 1, 2, or 3.

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/mL polyriboadenylic acid. Approximately $2\times10^7$ cpm (specific activity $4-9\times10^8$ cpm/µg) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at ($T_m$ less 10° C.) for the oligonucleotide probe. The membrane is then exposed to auto-radiographic radiographic film for detection of hybridization signals.

Stringent conditions means hybridization will occur only if there is at least 90% identity, preferably at least 95% identity and most preferably at least 97% identity between the sequences. Further, it is understood, for example, that a section of a 100 bps sequence that is 95 bps in length has 95% identity with the 1090 bps sequence from which it is obtained. See J. Sambrook et al., *Molecular Cloning, A Laboratory Manual*, 2d Ed., Cold Spring Harbor Laboratory (1989) which is hereby incorporated by reference in its entirety.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

The present invention relates to polynucleotides which differ from the reference polynucleotide such that the differences are silent, for example, the amino acid sequence encoded by the polynucleotides is the same. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand.

Thus, the term "polynucleotide encoding an enzyme (polypeptide)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzymes having an amino acid sequences as set forth in SEQ ID No.: 1, 2 or 3. The variant of the polynucleotide may be a naturally occurring allelic variant of the polynucleotide or a non-naturally occurring variant of the polynucleotide.

Thus, the present invention includes polynucleotides encoding a mature enzyme or polypeptide characterized as having thermostable carboxypeptide activity as well as variants of such polynucleotides which variants encode for a fragment, derivative or analog of the enzyme or polypeptide. Such nucleotide variants include deletion, substitution, addition, and insertion variants.

Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. In fact, probes of this type having at least up to 150 bases or greater may be preferably utilized. A probe may also be used to identify a DNA clone corresponding to a full length transcript and a genomic clone or clones that contain the complete gene including regulatory and promotor regions, exons and introns. An example of a screen comprises isolating the coding region of the gene by using a known DNA sequence to synthesize an oligonucleotide probe. Labeled oligonucleotides having a sequence complementary or identical to that of the gene or portion of the gene sequences of the present invention are used to screen a library of genomic DNA to determine which members of the library the probe hybridizes to.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme and which contain a sequence as set forth in SEQ ID Nos 1, 2, or 3. In referring to identity in the case of hybridization, as known in the art, such identity refers to the complementarity of two polynucleotide segments.

Alternatively, the polynucleotide may have at least 15 bases, at least 30 bases, and more preferably at least 50 bases which hybridize to any part of a polynucleotide of the present invention and which has an identity thereto (e.g., encoding amino acid sequences as set forth in SEQ ID Nos. 1, 2, or 3), as hereinabove described, and which may or may not retain activity. For example, such polynucleotides may be employed as probes for further identifying, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes a thermostable carboxypeptidase of the present invention. Further, the present invention is directed to polynucleotides having at least a 70% identity, preferably at least 90% identity and more preferably at least a 95% identity to a polynucleotide which encodes a an amino acid sequence as set forth in SEQ ID NOS: 1, 2, or 3, as well as fragments thereof.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phophatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization of simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5-flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture) Depending upon the host employed in a recombinant production procedure, the enzymes of the present invention may be glycosylated or may be non-glycosylated. Enzymes of the invention may or may not also include an initial methionine amino acid residue.

Antibodies generated against the enzyme or polypeptide corresponding to a sequence of the present invention can be obtained by direct injection of the enzyme or polypeptide into an animal or by administering the enzyme or polypeptide to an animal, preferably a nonhuman. The antibody so obtained will then bind the enzyme or polypeptide itself. In this manner, even a sequence encoding only a fragment of the enzyme or polypeptide can be used to generate antibodies binding the whole native enzyme or polypeptide. Such antibodies can then be used to isolate the enzyme or polypeptide from cells expressing that enzyme or polypeptide.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA") , defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of V$_H$ and V$_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise V$_H$ and $_L$V chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: a Companion to Methods in Enzymology*, Vol. 2, page 97, 1991; Bird et al., *Science* 242:423–426, 1988; Ladner et al., U.S. Pat. No. 4,946,778; Pack et al., *Bio/Technology* 11:1271–77, 1993; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106, 1991.

Antibodies can be prepared using an intact polypeptide or fragments containing small peptides of interest as the immunizing antigen. The polypeptide or a peptide used to immunize an animal can be derived from translated cDNA or chemical synthesis which can be conjugated to a carrier Protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991, incorporated by reference).

The monoclonal antibody which binds a peptidase or a biologically active fragment thereof can be utilized alone, or in combination with another agent.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against an enzyme of the present invention may be used in screening for similar enzymes from other organisms and samples. Such screening techniques are known in the art, for example, one such screening assay is described in Sambrook and Maniatis, Molecular Cloning: A Laboratory Manual (2d Ed.), vol. 2:Section 8.49, Cold Spring Harbor Laboratory, 1989, which is hereby incorporated by reference in its entirety.

The enzyme or polypeptide of the present invention is useful in sequencing reactions. Protein sequencing is an integral component of modern biochemical research. Edman degradation is useful for N-terminal sequencing, but it fails when the amino terminus is chemically protected. Aside from endoproteolytic fragmentation, another way to obtain sequence information from proteins is to sequence from the C-terminus. Various C-terminal sequencing methods have been developed: chemical cleavage analogous to Edman degradation (Hardeman et al., supra (1998)), and enzymatic digestion by carboxypeptidases (Thiede et al., (1997), which is incorporated herein by reference). A particularly powerful approach is enzymatic ladder sequencing, in which a carboxypeptidase is used to generate a set of differentially cleaved peptides that can be visualized in a mass spectrum; mass differences between adjacent peaks correspond to the molecular masses of individual amino acids that have been released. Enzymatic protein ladder sequencing has the potential to sequence as far as the enzyme can cut. However, a number of difficulties have limited the applicability of this approach: i) the limited specificities of a given carboxypeptidase toward the 20 common amino acids; and ii) the resistance of native protein molecules to digestion at mesophilic temperatures.

Accordingly, due to the thermostability of the present polypeptide (e.g., the thermostable carboxypeptidase), the polypeptide is useful in performing C-terminal sequencing reactions above mesophilic temperatures. As more fully described below, the present invention provides a method for determining an amino acid sequence of a polypeptide by contacting a polypeptide with a thermostable carboxypeptidase of the invention, wherein the carboxypeptidase hydrolyzes peptide bonds. Such methods include contacting a polypeptide with a thermostable carboxypeptidase of the invention at temperatures above 65° C., and preferably at about 90° C. The ability to hydrolyze of peptide bonds increases at higher temperatures due to the unfolding or denaturation of the polypeptide to be analyzed. In one aspect of the invention a polypeptide to be sequenced is contacted with a thermostable carboxypeptidase under conditions wherein the carboxypeptidase hydrolyzes the peptide bonds of the polypeptide. The polypeptide fragments (i.e., the enzymatic products), include amino acids and peptides. Such amino acids and peptides can then be further sequenced or analyzed. Further sequencing reactions may employ additional enzymes, for example those used in N-terminal Edman degradation techniques, or may utilize the carboxypeptidase of the present invention. The products can be analyzed by any number of means including by mass spectrometry, HPLC, and other techniques know to those of skill in the art.

In another aspect of the invention, the thermostable protease may be used in bioremediation. Modern industry generates many pollutants for which the environment can no longer be considered an infinite sink. Naturally occurring microorganisms are able to metabolize thousands of organic compounds, including many not found in nature (e.g xenobiotics). Bioremediation, the deliberate use of microorganisms for the biodegradation of man-made wastes, is an emerging technology that offers cost and practicality advantages over traditional methods of disposal. The success of bioremediation depends on the availability of organisms that are able to detoxify or mineralize pollutants. Microorganisms capable of degrading specific pollutants can be generated by genetic engineering and recursive sequence recombination.

Although bioremediation is an aspect of pollution control, a more useful approach in the long term is one of prevention before industrial waste is pumped into the environment. Alternatively, the enzyme of the present invention can be used to convert a toxin in the environment to a non-toxic form or convert a non-toxic substance to a more useable substance. Furthermore, the enzyme of the invention (i.e., the thermostable metallo-carboxypeptidase) can be used to speed up the remediation of a particular substance in the environment. For example, exposure of recombination-generated microorganisms capable of degrading polypeptides, such as toxins or pollutants would result in detoxification. Issues of releasing recombinant organisms can be avoided by containing them within bioreactors fitted to the industrial effluent pipes. This approach would also allow the microbial mixture used to be adjusted to best degrade the particular wastes being produced. Finally, this method would avoid the problems of adapting to the outside world and dealing with competition that face many laboratory microorganisms.

In another aspect of the invention, the thermostable carboxypeptidase may be used in food processing for degredation of peptides into amino acids or polypeptides to peptides and amino acids. Such degradation can be used to synthesize food products or to generate intermediates in the generation of food products. For example, L-glutamic acid is best known as a flavor enhancer for human food. L-lysine and L-methionine are large volume additives to animal feed and human supplements. L-tryptophan and L-threonine have similar potential applications. L-phenylalanine and L-aspartic acid have very important market potential as key components in the manufacture of the low-calorie sweetener aspartame, and other promising low-calorie sweeteners have compositions containing certain amino acids as well. Infusion solutions require a large range of amino acids including those essential ones in human diets.

The present invention will be further described with reference to the following examples; however, it is to be understood that the present invention is not limited to such examples.

EXAMPLE

Chemicals and Reagents: All chemicals were of reagent grade and were obtained from the following sources: yeast extract and tryptone from Difco (Detroit, Mich.); Iysozyme, Dnase-I and PMSF from Sigma (St. Louis, Mo.); glycerol and DTT from ICN Biomedical (Aurora, Ohio); column chromatographic resins from Amersham Pharmacia Biotech (Piscataway, N.J.); hydroxyapatite from American International Company (Natick, Mass.); argon gas from Air Liquide (Houston, Tex.); Amicon YM10 membranes and Microcon 3 ultrafiltration units from Millipore (Bedford, Mass.); SDS-PAGE gels, Mark-12 marker proteins, and PVDF membrane from Novex (San Diego, Calif.); Tris-Cl base from Boehringer Mannheim (Indianapolis, Ind.); ammonium sulfate from Mallinckrodt (Paris, Ky.); $Na_2EDTA$ dihydrate from Fluka (Ronkonkoma, N.Y.); and NaCl from Fischer (Fair Lawn, N.J.). Amido black, KMES buffer, free amino acids, $CoCl_2$, ninhydrin and N-acetyl renin substrate were also purchased from Sigma. All ZAX N-blocked dipeptides were purchased from Bachem Torrance, Calif.). $CoCl_2$ and TFA were obtained from Mallinckrodt. Polypropylene microcentrifuge tubes were purchased from Eppendorf (Westbury, N.Y.). Bovine serum albumin standard solution was purchased from Pierce (Rockford, Ill.). $ZnCl_2$ was purchased from EM Science (Gibbstown, N.J.).

Example 1

Cell Culture and Cell Extracts

Archaeal Strain and Culture Conditions: *Pyrococcus furiosus* strain DSM 3638 was obtained as a lyophilized culture from the Deutsche Sammlung von Microorganismen und Zellkulturen, Braunschweig, Germany. *P. furiosus* was grown at 90° C. under strictly anaerobic conditions. The archaeon was revived on a complex medium and scaled up in a 450 liter fermentor at the Fermentation Facility, University of Wisconsin (Madison, Wis.). After sterilization, the fermentor was cooled down to 90° C. Solid cysteine hydrochloride was added a few hours before inoculation at a final concentration of 0.4 $g.l^{-1}$ to pre-reduce the medium. Growth was monitored by measuring the optical density at 600 nm. Cells were harvested at late log phase ($\Delta$ OD.~0.6 in 12 h) with a Sharples continuous centrifuge. The cell paste was frozen immediately in liquid $N_2$ and stored at −80° C. The approximate cell yield (wet weight) was 3 g/L.

Preparation of *P. furiosus* Cell Extract: Frozen *P. furiosus* cell paste (~450 g) was thawed out in 2 L of cell lysis buffer (see below) by incubating at room temperature for 30 minutes with gentle stirring. The cell lysate was then centrifuged at 12,000 rpm for 30 min at 5° C. in a Sorvall GSA rotor. The supernatant fractions were pooled, degassed, and 2 mM each of dithiothreitol and (DTT) sodium dithionite (DT) were added.

Buffers: The cell lysis buffer was composed of 50 mM Tris-Cl (pH 8.0); Dnase-I (10 mg/L); 5 mM $MgSO_4$; and 1 mM PMSF. Buffer A consisted of 50 mM Tris-Cl (pH 8.0); 1 mM EDTA; 1 mM PMSF; 2 mM DTT and 10% glycerol. Buffer B was the same as buffer A but without DTT. The pH of all buffers was adjusted at room temperature. The buffers were degassed, sparged with argon gas, and maintained under positive argon pressure.

Example 2

Purification of PfuCP

Purification of PfuCP: The *P. furiosus* crude extract (8 $U.mg^{-1}$; 21,400 mg) was loaded at a flow-rate of 20% of 9 ml. $min.^{-1}$ onto a QFF column (10×30 cm) previously equilibrated with buffer A. Elution was performed over 700 minutes at a flow rate of 9 $ml.min^{-1}$ with a gradient of 0–0.5 M NaCl in the same equilibraton buffer. QFF fractions between 0.25–0.36 M NaCl containing PfuCP activity (46 $U.mg^{-1}$) were pooled and suspended in EDTA-free Tris-Cl buffer (pH 6.5) to a total volume of 1220 ml. Dilution of EDTA was achieved by Amicon ultrafiltration through a YM10 membrane (10 kDa cutoff) and the volume was reduced to 75 ml. This procedure was repeated twice and then the combined fractions were diluted to a final volume of 1125 ml and loaded onto a hydroxyapatite column (XK50 column; 50×10 cm) that was pre-equilibrated with 50 mM Tris-Cl (pH 6.5) at a flow rate of 5 $ml.min^{-1}$. Elution was performed over 420 minutes with a linear gradient of 0–0.5 M potassium phosphate in Tris-Cl buffer (pH 8.0) at a flow rate of 5 $ml.min.^{-1}$. Fractions with the highest activity were pooled (133 $U.mg^{-1}$; 750 mg) and diluted with buffer A. Ammonium sulfate was then added to a final concentration of 10% (w/v) in a final volume of 500 ml and loaded at 50% of 5 $ml.min^{-1}$ over 280 minutes with a gradient of 7–0% ammonium sulfate. Fractions with a specific activity of 452 $U.mg^{-1}$ (183 mg) were pooled and diluted in buffer A to a final volume of 780 ml and loaded at 50% of 6 $ml.min^{-1}$ onto a 50 ml Q-Sepharose High-Performance Column (QHP; XK26/10) previously equilibrated with buffer A. Elution was performed at 6 $ml.min^{-1}$ over 65 minutes with a gradient of 0.1–0.5 M NaCl in buffer A. QHP fractions containing highest activity were pooled (1131 U. $mg^{-1}$; 14 mg) and exchanged with buffer B. The protein sample was concentrated by Amicon filtration and loaded onto a Superdex G-200 gel filtration column (XK60 column; 26×58 cm) at a flow rate of 2 $ml.min^{-1}$ in buffer A containing 0.25 M NaCl. Elution was monitored by the UV absorbance at 280 nM. The fractions with highest activity (1303 $U.mg^{-1}$; 13 mg) were pooled and loaded onto a MonoQ column pre-equilibrated with buffer B. Elution was performed at 1 $ml.min^{-1}$ over 60 minutes with a gradient of 0–0.35 M NaCl in equilibration buffer. Pure PfuCP fractions (1391 $U.mg^1$; 11 mg), as determined by SDS-PAGE, were pooled and stored at −80° C.

SDS-PAGE: SDS-polyacrylamide gel electrophoresis was performed in 12% Tris-glycine gels according to established procedures. For reducing conditions, samples were prepared in 0.1% SDS sample buffer containing 2 mM DTT; for reducing and denaturing conditions, samples were also pre-incubated at 80° C. for 1 min prior to electrophoresis at 125 $V.cm^{-1}$ for about 2 hours. The gels were stained overnight in collodal Coomassie stain and destained in distilled water. Mark-12 protein markers were used to calibrate the gels and a second order polynomial function was used to calculate the apparent molecular weights.

Gel Filtration: The native molecular weight of PfuCP was determined by gel filtration at room temperature using a Superdex 200 column (1.6×60 cm; Pharmacia-LKB) connected to an FPLC. The column was calibrated with the following standards: blue dextrin, thyroglobulin, ferritin, catalase, aldolase, bovine serum albumin and carbonic anhydrase. To avoid anomalous migration behavior of proteins within the gel matrix, gel filtration was performed in the presence of 0.2 M NaCl in 50 mM Tris-Cl buffer (pH 8.0) at a flow rate of 0.5 $ml.min^{-1}$.

MALDI-TOF Mass Spectrometry: The molecular weight of the purified apoPfuCP was determined by matrix-assisted laser desorption ionization time-of-flight mass spectrometry. Purified PfuCP in Tris buffer was exchanged three times with distilled water through Microcon ultrafiltration. Sinapinic acid was used as the matrix and 4.5 pmol of apoPfuCP was loaded. The ELITE mass spectrometer (PerSeptive Biosystems, Inc., Framingham, Mass.) was operated in linear mode with an acceleration voltage of 25 kV using delayed extraction; 63 scans were averaged.

Protein Sequence Analysis: Following reducing and denaturing SDS-PAGE, the monomeric apoPfuCP band was electroblotted onto a 0.2 µm polyvinylidenedifluoride (PVDF) membrane for 3 hours at 38 V. The membrane was stained with amido black for ca. 5 min. and then destained in deionized water; the PfuCP band was cut out and subjected to N-terminal sequencing (Perkin Elmer 476; Applied Biosystems, Foster City, Calif.). In situ Endo-Lys C digestion was performed on the PVDF membrane according to the established procedures. The lyophilized digest was resuspended in minimal buffer (2% acetonitrile, 0.057% trifluoroacetic acid) and injected onto a Reliasil C18 column (0.5×100 mm) at 35° C.; a linear gradient of 9–54% B (90% acetonitrile, 0.04% TFA) was performed at a flow rate of 10 $\mu$L.min$^{-1}$ over 45 minutes; peptides were monitored at 200 nM. Two major peaks collected at 5–10% gradient were then subjected to MALDI-TOF MS analysis followed by N-terminal sequencing.

Example 3

Enzymatic Activity

Figure 11:
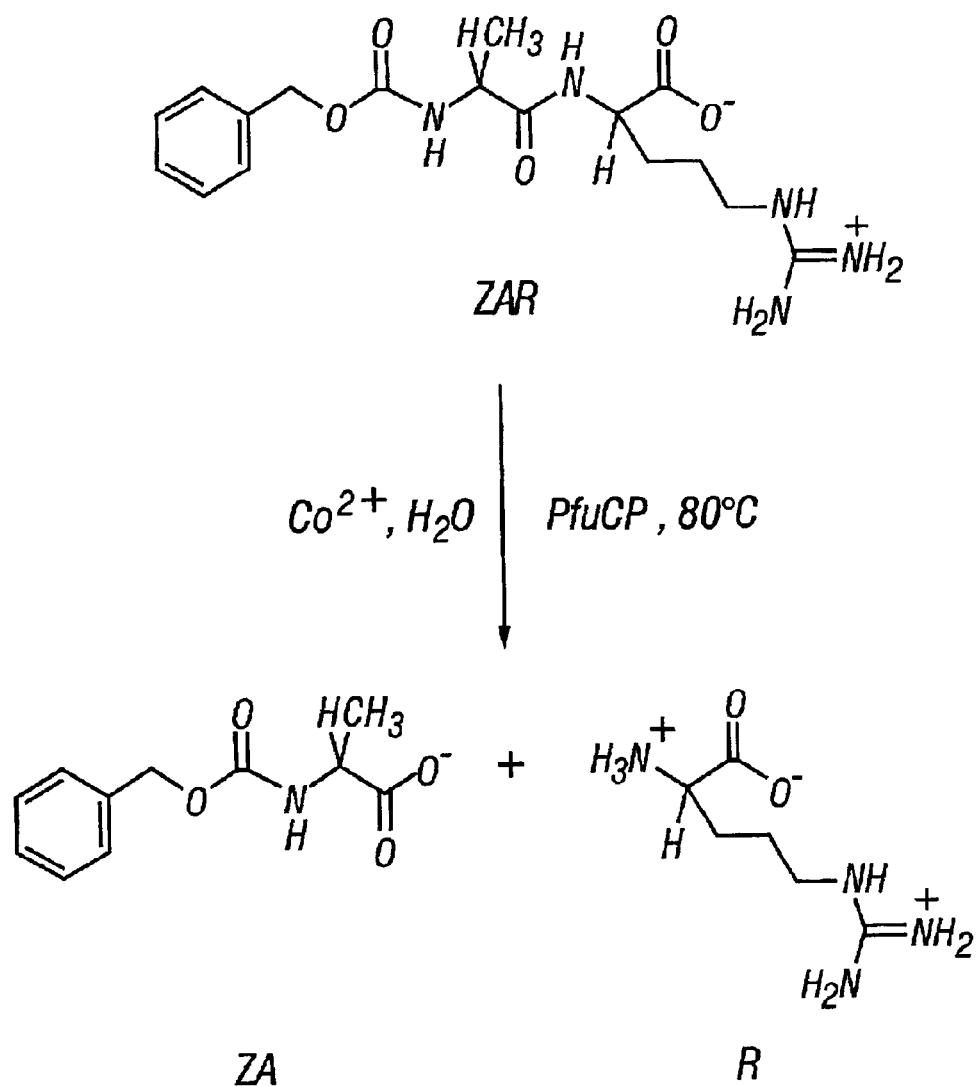
FIG. 11 shows the hydrolysis of ZAR.

Assay of Enzyme Activity: Unless stated otherwise, enzymatic activity was assayed using 4 $\mu$l of enzyme sample in a total volume of 100 $\mu$l of 0.1 M KMES buffer (pH 6.5), starting with 2 mM ZAR in the presence of 0.4 mM CoCl$_2$. Polypropylene microcentrifuge tubes were used. The enzyme and substrate were mixed quickly at room temperature and then brought to 80° C.; the equilibration time for the reaction mixture to reach 80° C. was considered negligible relative to the time scale of the assay. The reaction mixture was incubated at 80° C. in a water bath (Neslab EX-200 DD) for 10 minutes followed by quenching on ice. Subsequently, 750 $\mu$l of cadmium-ninhydrin reagent (21) was added and the samples were incubated for an additional 5 min at 80° C. for color development followed by quenching on ice. The absorbance was read at 500 nm (HP 8452A diode array spectrophotometer) with an unheated assay mixture containing Cd-ninhydrin reagent serving as the blank. Absorbances were compared with an arginine standard curve in order to calculate specific activities. Stock solutions of ZAR and CoCl$_2$ were prepared in 0.1 M KMES buffer (pH 6.5), and when necessary, dilution of enzyme samples was done in 50 mM Tris-Cl buffer (pH 8.0). All pH adjustments were performed at room temperature. The hydrolysis of ZAR by PfuCP is shown in FIG. 11. The free amine of the liberated arginine reacts with ninhydrin to yield the chromophore, Ruheman's purple (absorbance at 500 nM).

One unit of activity is defined as the amount of enzyme required to generate one $\mu$mole of arginine from ZAR in one minute at 80° C. Activity assays for other ZAX amino acid substrates (X=A, D, E, F, G, H, I, K, L, M, N, P, R, S, V, W, Y) were performed under otherwise identical assay conditions; appropriate amino acids were used to prepare standard curves. Spontaneous hydrolysis of the synthetic substrates was not observed at these temperatures. Protein concentrations were quantified by the Bradford assay using bovine serum albumin as the standard.

Example 4

Characterization of PfuCP

Re-activation by Metal Ions: The divalent metal ion dependence of PfuCP activity was examined by performing the enzymatic assay at various concentrations of Co$^{2+}$ and Zn$^{2+}$ under otherwise standard conditions. The metal chlorides were prepared in 0.1 M KMES buffer (pH 6.5). Prior to use, purified PfuCP was diluted 500-fold in the same buffer. Data fitting for these and other experiments was done using Microcal Origin 5.0 (Northhampton, Mass.).

Temperature and pH Optima of PfuCP Activity: The temperature optimum of PfuCP was determined by measuring the activity at various temperatures from 20 to 100° C. with saturating concentrations of ZAR (11.75 mM) but under otherwise standard assay conditions. Similarly, the pH optimum of the activity was determined by measuring the activity at various pH ranges using the following buffers; piperazine, 4.8–6.2; KMES, 5.3–6.9; MOPS 6.5–7.5; and HEPES, 6.9–8.0. The pH of all buffers was adjusted at room temperature.

Far UV-CD Spectroscopy: Changes in the secondary structures of PfuCP were monitored in the far-UV range from 190–300 nM in 10 mM potassium phosphate buffer (pH 7.0) on an Aviv Circular Dichroism Spectrometer (model 62A-DS). Room temperature experiments were performed at 26° C. on apoPfuCP (15 $\mu$M) and after reconstitution with 1 mM CoCl$_2$. The spectrum of the Co$^{2+}$-treated sample was also examined at 80° C. The results were expressed as molar residue ellipticity (deg.cm$^2$.dmol$^{-1}$).

Fluorescence Spectroscopy: The intrinsic fluorescence properties of PfuCP were determined using a Hitachi F-4500 fluorescence spectrophotometer. The excitation wavelength used was 290 nM, and the emission spectrum was monitored from 300–450 nM. The scan speed was 60 min$^{-1}$ and the photomultiplier voltage was set at 700. All the experiments were performed in 10 mM potassium phosphate buffer (pH 7.0). After measuring the fluorescence intensity of apoPfuCP at room temperature, Co$^{2+}$ was added to a final concentration of 1 mM and incubated for 5 min; measurements were then made at both room temperature and 80° C. In a separate experiment, the reversibility of the temperature-dependent changes was examined by monitoring the fluorescence intensity as CoPfuCP was heated from 25 to 85° C. and then after cooling back down to room temperature.

Thermal Inactivation: PfuCP (730 nM in 0.1 M KMES buffer, pH 6.5) was incubated in the presence and absence of 0.4 mM Co$^{2+}$ at 80° C. for various time points up to 120 min. Activity was then measured under standard assay conditions. Residual activity was calculated as the fraction of remaining activity relative to that of an unheated enzyme sample maintained on ice.

Example 5

Sequencing with PfuCP

C-terminal Ladder Sequencing of N-acetyl Renin Substrate with PfuCP: The sequencing reaction was carried out in polypropylene microcentrifuge tubes with the following reaction mixture in a total volume of 5 $\mu$l: 5 mM KMES buffer (pH 6.5), 50 $\mu$M porcine N-acetyl renin substrate (NARS), 0.4 mM CoCl$_2$, and 150 nM PfuCP. The samples were incubated at 80° C. in a water bath for 1 minute followed by quenching on ice and the addition of 0.1% TFA. Samples were analyzed by MALDI-TOF MS and the peaks assigned to within 0.3 Da of their monoisotopic masses. The mass differences between adjacent peaks were correlated with the molecular masses of released amino acid; although for an unknown sequence, leucine and isoleucine would be indistinguishable in the spectrum. The amino acid sequence of NARS (MW 1801.3) is: Ac-Asp-Arg-Val-Tyr-Ile-His-Pro-Phe-His-Leu-Leu-Val-Tyr-Ser. The amount of digested NARS loaded was approximately 13 pmol and the matrix used was α-cyanohydroxycinnamic acid. The acceleration voltage was 20 kV and 99 scans were averaged. Room temperature sequencing experiments were carried out at 20° C.

RESULTS

Purification: Initial studies on substrate hydrolysis showed that PfuCP was active towards hippuryl-arginine (N-Benzoyl-Gly-Arg), the substrate that was used to isolate a carboxypeptidase from Sulfolobus solfataricus. However, the Bz-Gly bond was susceptible to hydrolysis as evidenced by activity towards hippuric acid (Bz-Gly). Hence, an alternate set of substrates (ZAX) with a stable N-terminal amide bond was chosen to monitor activity. A control experiment showed no hydrolysis of ZA (N-Cbz-Ala), thus localizing PfuCP hydrolysis of ZAR to the C-terminal alanyl-arginine peptide bond, unequivocally demonstrating carboxypeptidase activity.

Preliminary small-scale experiments were performed to standardize the purification conditions, during which it was noted that PfuCP did not bind to the affinity matrix arginine-sepharose. To test for the presence of multiple carboxypeptidases, P. furiosus crude extract was passed through a QFF column and then the eluting carboxypeptidase activity was monitored with various ZAX substrates. Maximum activity was found in the same fraction for all of the substrates tested, suggesting that there is one distinct carboxypeptidase in P. furiosus. All activities of representative ZAX substrates (aliphatic, X=Ile; basic, X=Arg and Lys; aromatic, X=Phe and Trp; polar, X=Asn, Ser, and His) eluted in the same major peak. Significant loss of activity was observed in purification fractions over the course of 3–4 days at room temperature. Preliminary studies had shown that DTT and EDTA completely abolished carboxypeptidase activity in crude extract. In order to inhibit proteolytic and carboxypeptidase activity, 2 mM DTT, 1 mM EDTA, and 1 mM PMSF were added to purification buffers and PfuCP was purified in a metal-depleted, catalytically inactive form. Other observed losses in activity due to freeze-thawing of purification samples were prevented by the addition of 10% glycerol to samples stored at −20° C. Subsequent large-scale purification steps involving anion-exchange, hydroxyapatite, hydrophobic and gel filtration chromatographic procedures yielded 11 mg PfuCP from 21 g crude protein with a 174 fold purification and 9% recovery (Table 1). SDS-PAGE of the most active fractions in each purification step is shown in FIG. 1.

Figure 2:
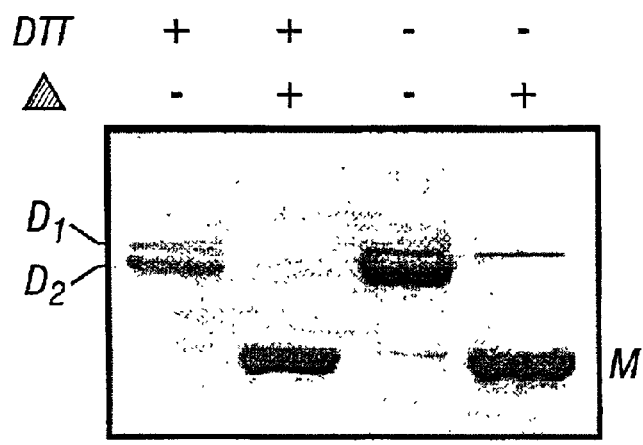
FIG. 2 shows oligomeric behavior of PfuCP. (A) Purified apoPfuCP was examined by SDS-PAGE under reducing or non-reducing conditions (in the presence or absence of 2 mM DTT), with or without pre-heating (Δ) at 80° C. Dimer bands, $D_1$ and $D_2$, appear at an apparent molecular mass of about 85 kDa while monomeric PfuCP (M) appears at 58 kDa. (B) Purified enzyme was exchanged twice with deionized water by ultrafiltration and then analyzed by MALDI-TOF MS in the presence or absence of 2 mM DTT.

Molecular Weight and Oligomeric State of PfuCP: Reducing and denaturing SDS-PAGE analysis (2 mM DTT and 80° C. pre-incubation for 1 min) showed a single band for purified monomeric PfuCP at a molecular mass of 58 kDa (FIG. 1). However, without heating at 80° C., PfuCP exists in two homodimeric forms ($D_1$, $D_2$ at ca. 85 kDa) of slightly different apparent molecular masses, both in the presence and absence of DTT (FIG. 2A, lane 1, 3). $D_1$ appears to be a DTT-sensitive dimeric form. When purified PfuCP is heated at 80° C. in the presence of 2 mM DTT, $D_1$ is monomerized along with D (FIG. 2A, lane 2). However when purified PfuCP is heated at 80° C. in the absence of DTT, $D_1$ remains intact while $D_2$ is monomerized to the 58 kDa band (FIG. 2A, lane 4). Interestingly, PfuCP is not expected to have cysteines (hence disulfides) based on its close homology to a putative, cysteine-less carboxypeptidase from the genome of the *hyperthermophilic archaeon, Pyrococcus horikoshii* (see below). One possible explanation for the DTT-sensitive dimeric form is that residual metal ions in the purification buffers may act to stabilize $D_1$; this stabilization is destroyed when DTT acts to chelate these ions.

Gel filtration at room temperature confirmed a dimeric state of approximate molecular weight 128 kDa for PfuCP in the presence or absence of DTT (data not shown); however, D could not be distinguished from $D_2$. MALDI-TOF MS showed a predominantly monomeric PfuCP at 59 kDa with a trace of dimer at 118 kDa, in the presence or absence of DTT (FIG. 2B) Monomerization may have been induced by the conditions of the MALDI-TOF MS experiment (eg. laser irradiation, organic solvent in the matrix solution). N-terminal sequencing suggests a homogeneous preparation of purified PfuCP.

Molecular mass characterization studies on several hyperthermophilic proteins have shown that self-association (into higher states) is a ubiquitous phenomenon. Phosphoribosyl anthranilate isomerase (tPRAI) from *Thermatoga maritima* Sterner et al., Protein Sci. 5, 2000–2008 (1996), and 3-phosphoglycerate kinase (Pgk) from *P. furiosus* and *Methanothermus fervidus*, Hess et al., *Eur. J. Biochem.* 233, 227–237 (1995) exist as homodimers whereas they are monomeric in mesophiles, Kohloff et al, FEBS Lett. 383, 245–250 (1996). Similarly, triose phosphate isomerase (TIM) is a tetramer in *P. furiosus*, but a dimer in all mesophiles. Furthermore, ornithine carbamoyltransferase (OTCase) from *P. furiosus* exists as a dodecamer while the mesophilic OTCases isolated to date have been trimeric, Legrain et al., *Eur. J. Biochem.* 247, 1046–1055 (1997). These results have led to suggestions that quaternary structure in hyperthermophilic proteins may play an important role in thermostability. Additional structural investigations are underway to determine if this is the case for PfuCP.

Sequence Analysis: Edman sequencing of the N-terminus of PfuCP yielded 30 residues (Pfu-N), while sequencing of two Endo-Lys C peptide fragments yielded two internal amino acid sequences of 32 and 16 residues, respectively (Pfu-I and Pfu-II) (FIG. 3). A BLAST search of all three sequences revealed no significant homology to any known entries in protein databases. However, all three fragments matched with 90–100% sequence similarity to a putative carboxypeptidase sequence (PhoCP) from the genome of *Pyrococcus horikoshii*, Kawarabagashi et al., DNA Res. 5, 55–76 (1998). No potential glycosylation sites were found. Comparison of the PfuCP N-terminal sequence with that of the deduced PhoCP shows that PfuCP may also have a pro-sequence of 16 residues. This pro-sequence does not correspond to any of the currently known membrane-spanning or secretory signal sequences. PfuCP does not contain this sequence, which suggests that it undergoes post-translational processing. Studies of the pyrolysin from *P. furiosus* showed the occurrence of a 26-residue signal sequence. Interestingly, pyrolysin is converted from a high molecular weight form (150 kDa) to a low molecular weight form (130 kDa) by autodigestion; this type of maturation is not likely in PfuCP as the molecular weight of PfuCP corresponds well with the size of the deduced PhoCP.

In the *T. aquaticus* carboxypeptidase, an HEXXH motif (where X is a non-conserved amino acid) has been found at positions 276–280, and both histidines have been determined to be catalytically relevant by mutagenesis and $Zn^{2+}$ binding studies. As the HEXXH motif typically occurs in endopeptidases and aminopeptidases, the carboxypeptidases from *T. aquaticus* was proposed to be the first member of a new class of carboxypeptidases. The presence of the same HEXXH motif in a similar position in PhoCP (residues 285–289) suggests that PfuCP may represent the second member of this new class of carboxypeptidases. Cloning and expression studies of the PfuCP gene are underway to further examine these issues.

Figure 4B:
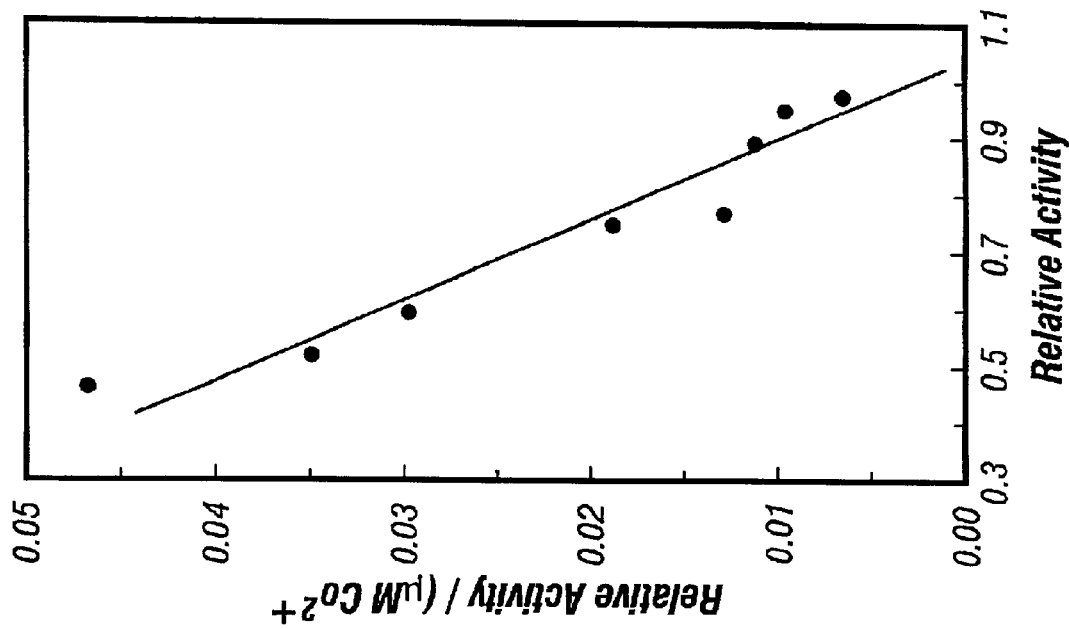
FIG. 4 shows the divalent metal ion dependence of PfuCP. (A) Activity assays were performed under standard conditions while the concentration of reconstituting divalent metal ion was varied: $Co^{2+}$ (●); $Zn^{2+}$ (○). Samples were pre-incubated on ice with metal ions for 1 hour. Data shown represent the average of duplicate values. (B) Linear reciprocal plot of binding data for $Co^{2+}$.
Figure 4A:
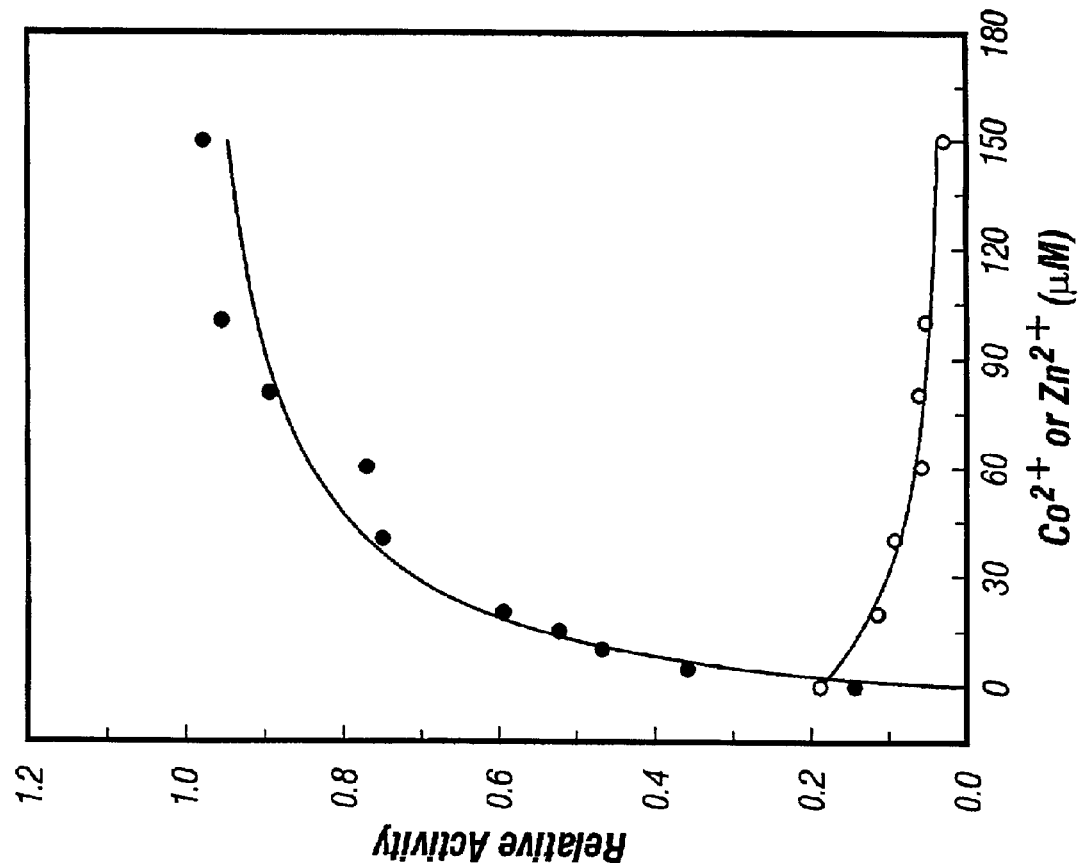

Metal Ion Reactivation: Although EDTA was used in the purification of PfuCP, apoPfuCP exhibited residual activity (ca. 14–19%) upon dilution prior to re-activation with $Co^{2+}$. As the final enzyme concentration was approximately 1 nM, even small amounts of adventitious metal ions in the buffer or incomplete removal of native metal ions might account for this residual activity; thus, apoPfuCP is taken to mean metal-depleted enzyme. Re-activation of apoPfuCP by $Co^{2+}$ followed simple hyperbolic behaviour (FIG. 4A). A linear reciprocal plot gives a binding constant (Kd) at 80° C. of 13±3 µM for $Co^{2+}$ and is consistent with one molecule of PfuCP (FIG. 4B). PfuCP activity was not observed in the presence of either 1 mM EDTA or 2 mM DTT. Even after extended incubation (up to 24 hours), the inhibition was found to be fully reversible upon 50-fold dilution and re-activation by $Co^{2+}$. The serine protease inhibitor PMSF had no effect on activity at a concentration of 1 mM. Thus, PfuCP is a metallocarboxypeptidase. Similar to apoPfuCP, apocarboxypeptidase purified from *Thermus aquaticus* is activated by $Co^{2+}$. However, when the *T. aguaticus* carboxypeptidase was expressed in *E.coli*, it was found to contain one g atom of $Zn^{2+}$ $mol^{-1}$ enzyme. Further studies are underway to determine the nature of metal ion site(s) in native PfuCP.

Optimal Temperature and pH Range for Activity: The activity of PfuCP exhibits a linear temperature dependence from 40–100° C. (FIG. 5A) and the optimum temperature observed is 90–100° C. The activation energy ($E_a$) and $Q_{10}$ value calculated from activity data between 59 and 93° C. were 47.8 $kJ.mol^{-1}$ and 1.19, respectively (FIG. 5B). Activity was not measured above 100° C. and no activity was observed at temperatures less than 40° C. under standard conditions. However, C-terminal ladder sequencing studies showed that PfuCP is active against peptide substrates at room temperature, suggesting that the ninhydrin assay was simply not sensitive enough to detect low rates of substrate turnover. The carboxypeptidases reported from *T. aquaticus* and *S. solfataricus* have temperature optima at 80 and 85° C., respectively Lee et al., Biosci. Biotechnol. Biochem. 56, 1839–1844 (1992); Colombo et al., Eur. J. Biochem. 206, 349–357 (1992). Thus, PfuCP has the highest optimal temperature for activity of any carboxypeptidase purified to date.

Figure 5C:
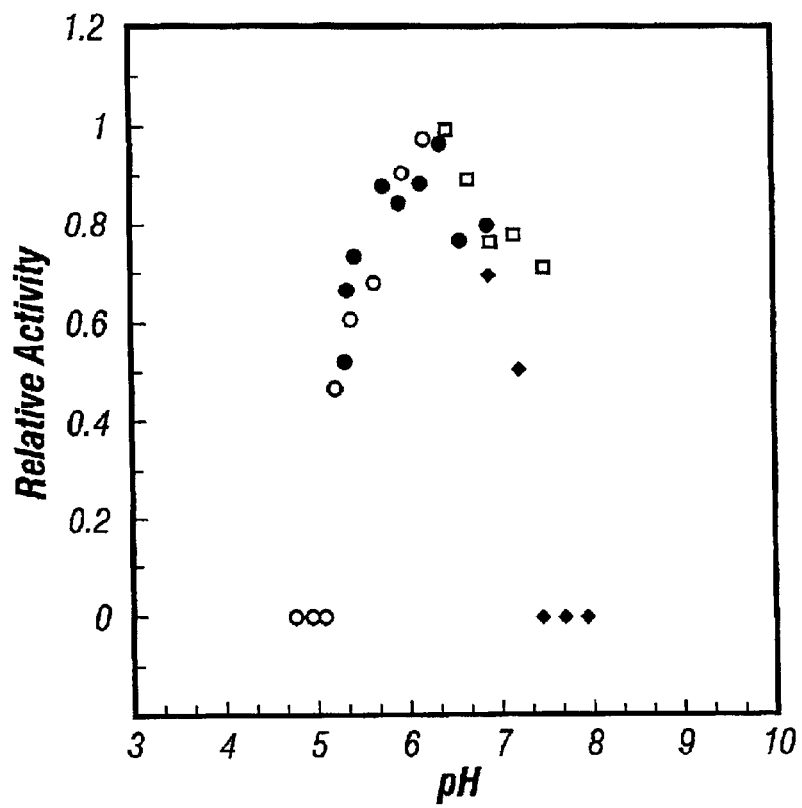
FIG. 5 shows the temperature and pH profiles of PfuCP activity. (A) Activity assays were performed under standard conditions as the sample temperature was increased from 20° C. to 100° C. Data shown represent an average of duplicate values and activity is normalized to the maximum activity at 100° C. (B) Arrhenius plot of temperature dependence data from 59–93° C. (C) Activity assays were performed under standard conditions with the following buffers: piperazine (○), pH 4.8–6.2; KMES (●), pH 5.3–6.9; MOPS (□), pH 6.5–7.5; HEPES (♦), pH 6.9–8.0. Data shown represent an average of duplicate values and activity is normalized to the maximum activity observed in 0.1 M MOPS (pH 6.5).

Unlike the hydrogenase from *P. furiosus* which exhibits an abrupt transition in the temperature profile from 60–70° C., the linear temperature dependence of PfuCP activity suggests that the enzyme does not undergo drastic conformational changes as the temperature is increased. Such linear temperature dependence has been observed with other proteolytic enzymes purified from *P. furiosus*, including prolyl endopeptidase and prolidase. This reflects the mechanistic simplicity of proteases in *P. furiosus* in comparison to its other enzymes. Furthermore, the pH optimum for PfuCP activity is between 6.2–6.5 using the substrate ZAR in the standard assay; the activity decreases sharply on either side of the pH profile (FIG. 5C).

Figure 6:
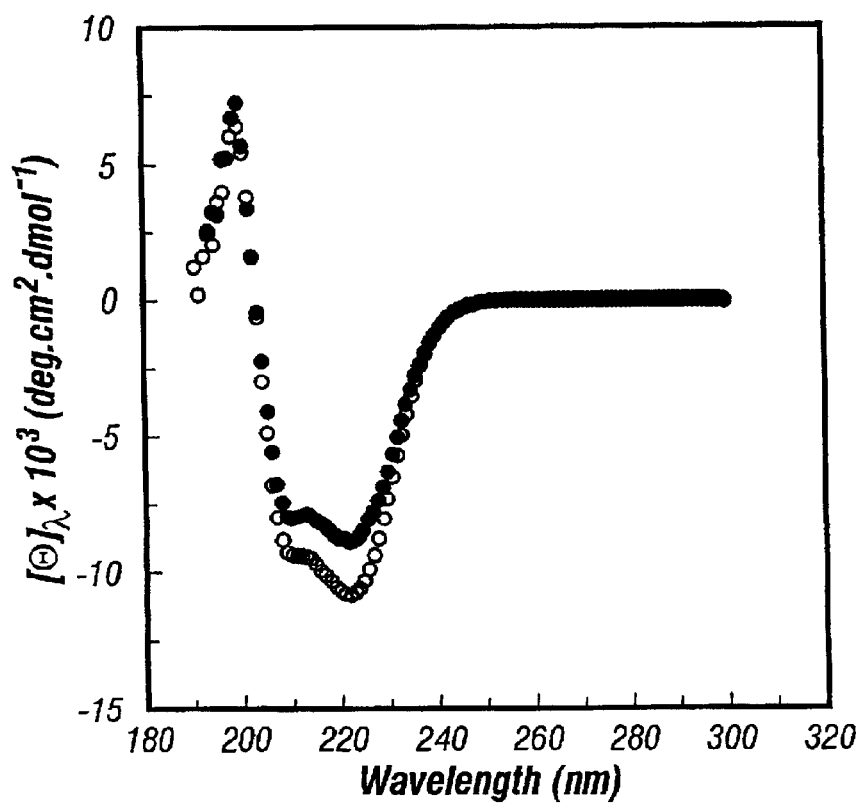
FIG. 6 shows far-UV circular dichroism spectra of PfuCP. Potential changes in the secondary structure of the purified PfuCP were monitored in 10 mM potassium phosphate buffer (pH 7.0). Spectra were recorded for the following: i) apoPfuCP at room temperature (○); ii) the $Co^{2+}$-incubated sample at 80° C. (●). Concentration of PfuCP was 15 µM. The spectra had two ellipticity minima at 222 and 210 nm, and a maximum at 199 nm.
Figure 7B:
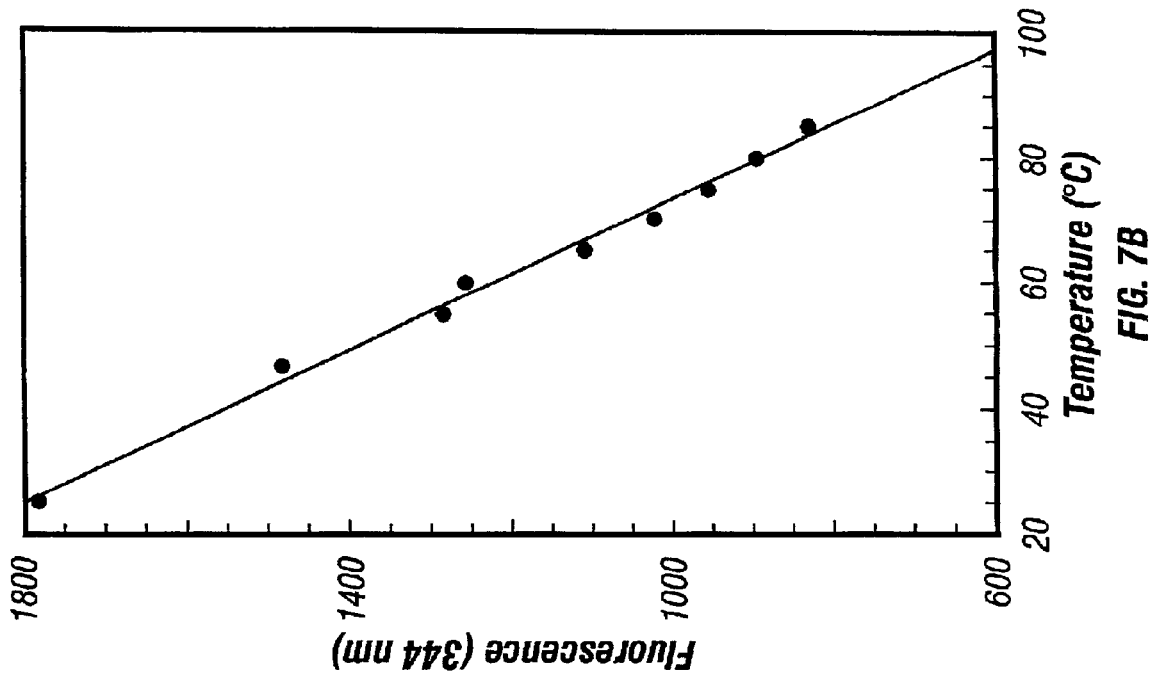
FIG. 7 shows the intrinsic fluorescence of PfuCP. (A) Comparison of emission spectra at 22 and 80° C. The following fluorescence spectra were recorded: i) apoPfuCP at 22° C. (○); ii) the $Co^{2+}$-incubated sample at 80° C. for 5 minutes (|). (B) fluorescence intensity as a function of temperature. Emission spectra were also recorded for the $Co^{2+}$-incubated sample at the following temperatures (° C.): 22, 47, 55, 60, 65, 70, 75, 80, and 85. The maximum excitation and emission wavelengths were 290 and 344 nm, respectively, and the bandwidth was 8 nm. Concentration of PfuCP for all fluorescence experiments was 15 µM.
Figure 7A:
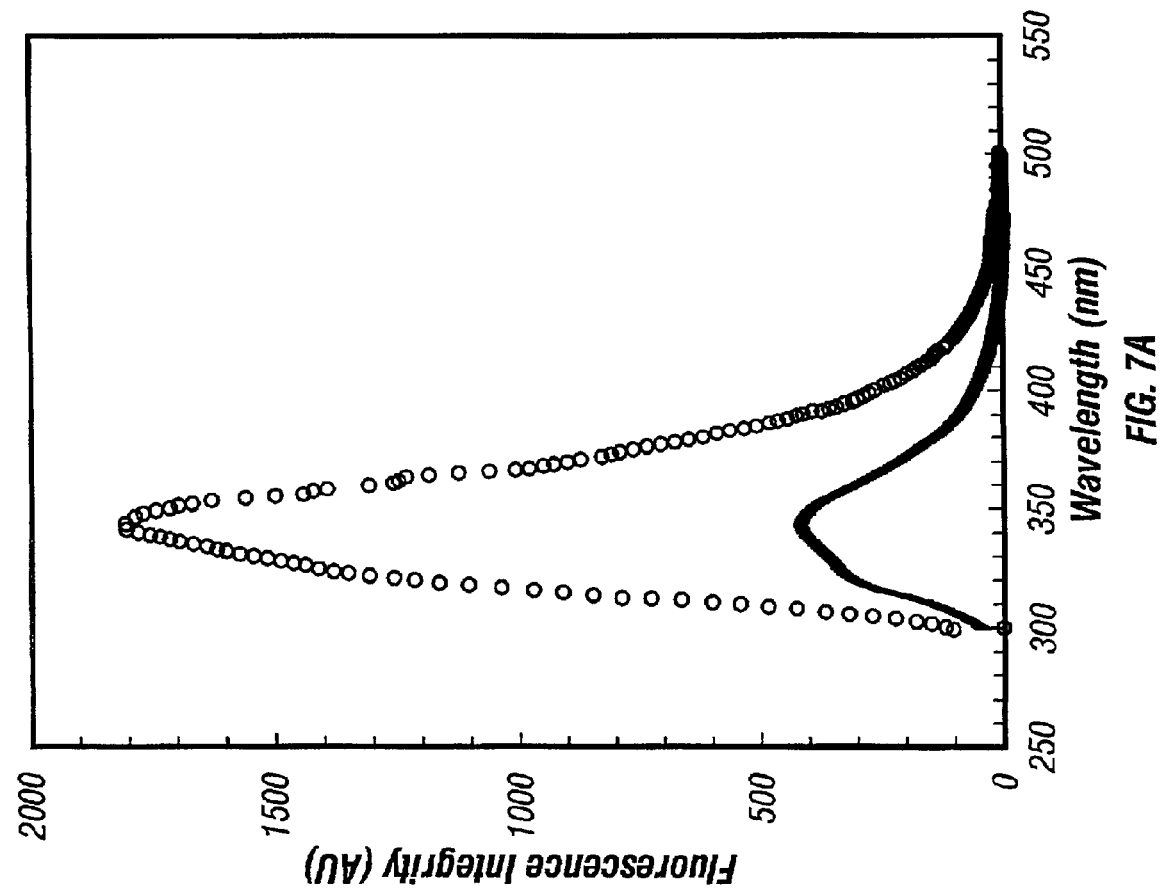

Structural Thermal Stability: At room temperature, both the intrinsic fluorescence intensity and far-UV CD spectrum of PfuCP remained unchanged following the addition of 1 mM $Co^{2+}$ to apoPfuCP, suggesting that the binding of $Co^{2+}$ had no significant effect on either global secondary structures or on local conformations of residues at the metal binding site (FIGS. 6, 7A). Carboxypeptidase A, a mesophilic metallocarboxypeptidase, also shows little difference between the native $Zn^{2+}$ containing enzyme and its apo form, the only difference being that the metal ligand, His 196, in the apoenzyme is rotated 110° about $\chi^2$ to salt bridge with Glu 270, another catalytically essential residue. As the temperature was increased to 85° C., the far-UV CD spectrum of PfuCP remained essentially the same in terms of overall features, with only a slight decrease in negative ellipticity from 205–230 nM. However, the intensity of the intrinsic fluorescence decreased linearly with increasing temperature ($\Delta$–17° $C.^{-1}$) without a noticeable shift in the wavelength of the emission maximum at 344 nM (FIG. 7B). This gradual quenching of the fluorescence follows the observed linear temperature dependence of activity (see above), indicating a smooth change in activity as opposed to a 'switch' operating at a threshold temperature. In hyperthermophilic enzymes, a gradual increase in activity with temperature has been correlated to increased flexibility in the overall structure Lenderman et al., J. Biol. Chem. 268, 24394–24401 (1993). In addition, the quenching of fluorescence is essentially reversed upon cooling to room temperature. The invariance in CD spectra and reversible quenching of intrinsic fluorescence suggest that PfuCP is structurally thermostable in the presence of $Co^{2+}$. Studies are underway to characterize the thermal stability and folding of the apoPfuCP.

Figure 8:
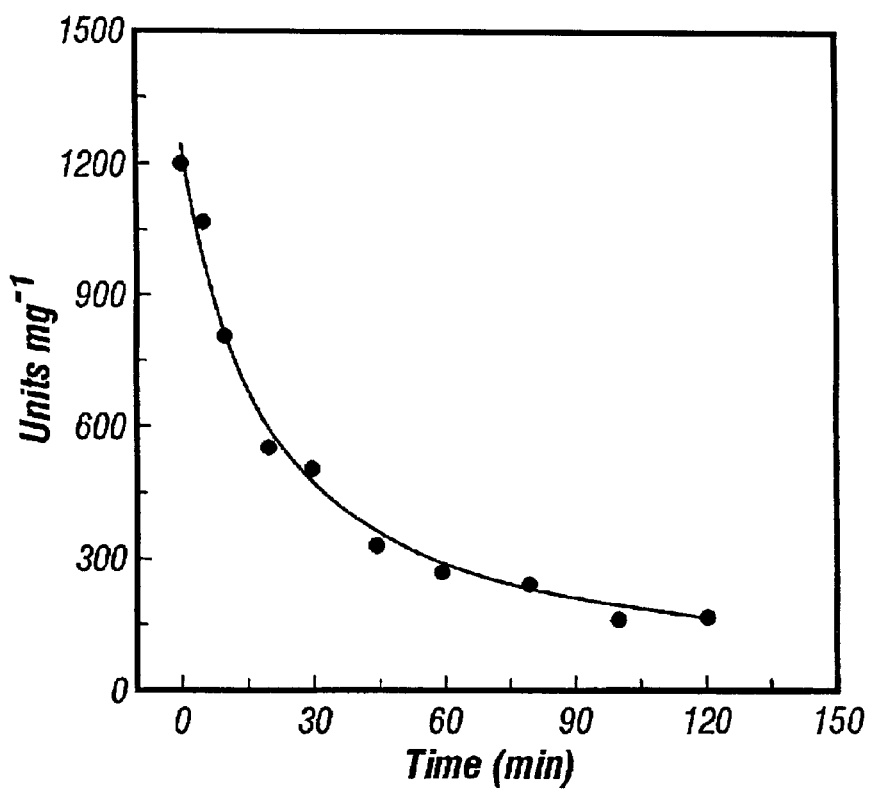
FIG. 8 shows the thermal inactivation of ApoPfuCP. ApoPfuCP (730 nM in 0.1 M KMES, pH 6.5) was pre-incubated at 80° C. for various time points and then residual activity was assayed under standard conditions. The residual activity was calculated as the fraction of the remaining activity relative to the unheated enzyme maintained on ice. Data points represent the average of duplicate values.

Thermal Inactivation: In contrast to the apparent structural thermostability of $Co^{2+}$—reconstituted PfuCP, the enzymatic activity showed an irreversible second-order decay during incubation at 80° C.; 50% activity remained after ca. 40 minutes and the second order decay constant was $2.0 \times 10^{-5} \pm 2 \times 10^{-6}$ $s^{-1}.mg.units^{-1}$ (FIG. 8). The kinetics do not appear to be first order, which might be expected if the rate-determining step of activity loss were simply 'metal-ion escape' from the binding site. The activity decay of CoPfuCP is essentially identical to that of apoPfuCP (FIG. 8). It is possible then that in vivo, PfuCP is stabilized by solutes such as cyclic-2,3-diphosphoglycerate in methanogens or di-myo-inositol-1,$1^2$-phosphate and mannosyl glycerate in *P. furiosus*. PfuCP heated at 80° C. in the presence of 0.4 mM $Co^{2+}$, for an hour shows no obvious fragmentation or autoproteolysis as determined by MALDI-TOF MS and SDS-PAGE.

Figure 9A:
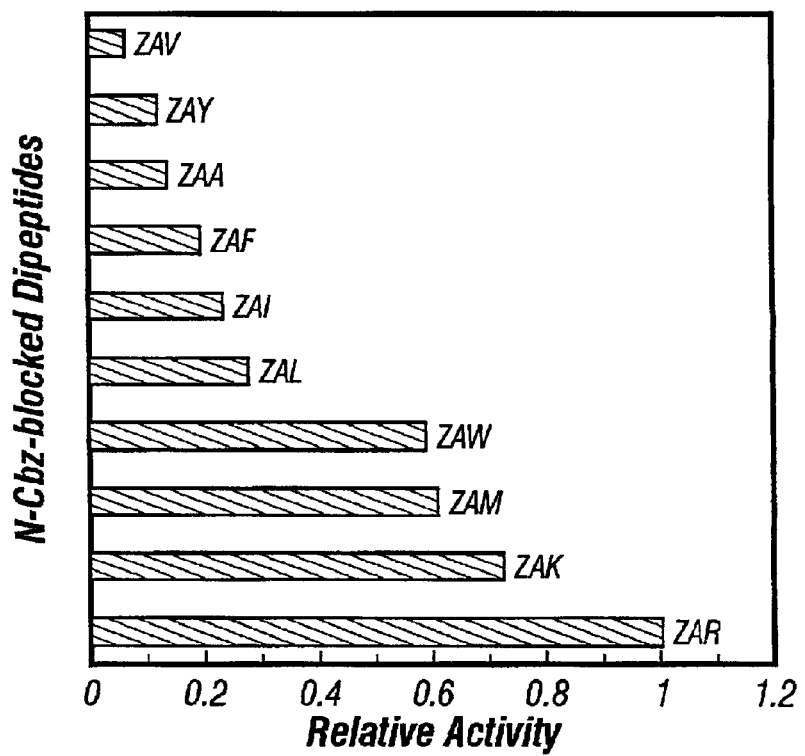
FIG. 9 shows the C-terminal specificities of PfuCP. (A) Activity assays were performed under standard conditions for the hydrolysis of a series of synthetic N-Cbz-alanyl-Xaa (ZAX) dipeptides. PfuCP shows a preference for basic, aliphatic and aromatic C-terminal amino acids. Activity against ZAS, ZAH, and ZAN was observed at longer digestion times (30 min). Data shown represent the average of triplicate values. (B) Activity assays were performed under standard conditions while varying the concentration of the N-blocked dipeptide ZAR. Data shown represent the average of duplicate values.
Figure 9B:
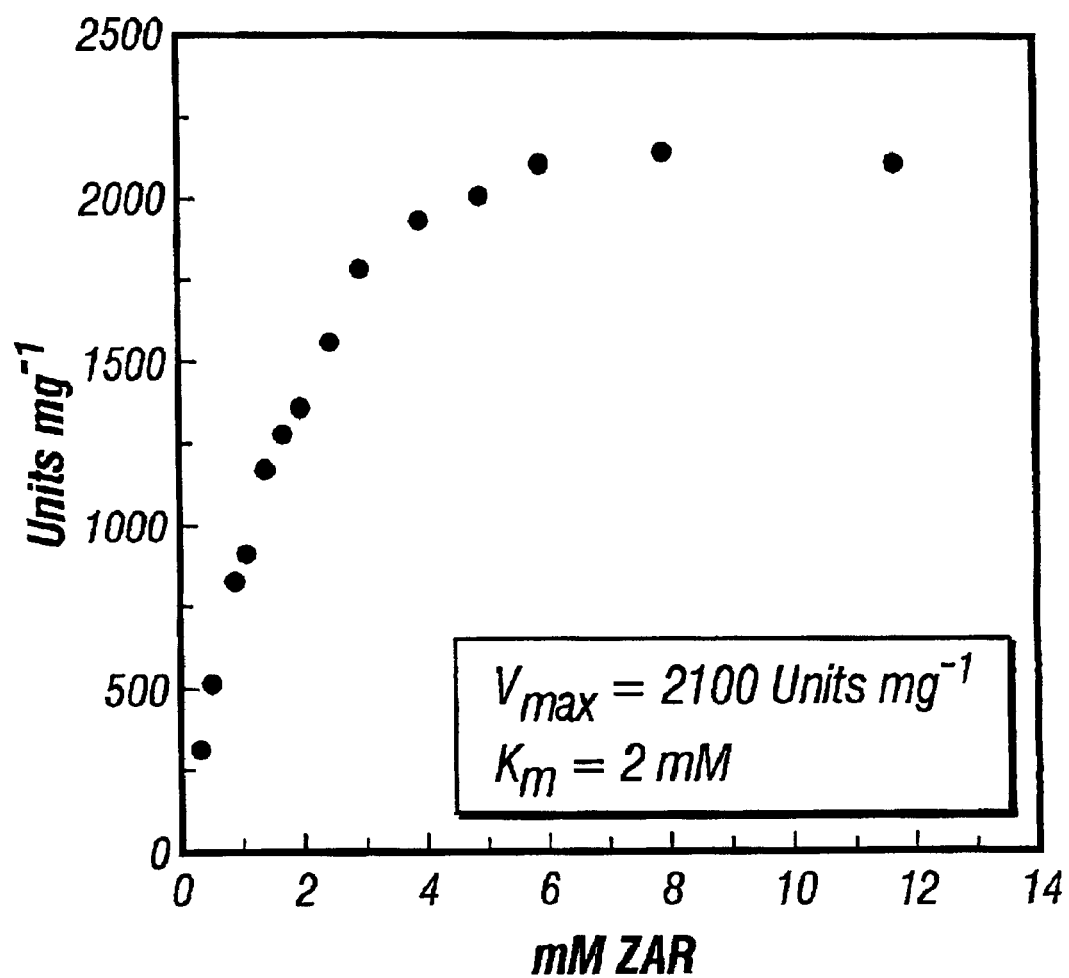

PfuCP C-terminal Specificities: PfuCP exhibits a relatively broad specificity for neutral, aliphatic, basic, polar, and aromatic C-terminal residues under standard assay conditions against synthetic N-Cbz-blocked dipeptide substrates; maximum activity occurs with a C-terminal arginine (FIG. 9A). This broad specificity of PfuCP may reflect the phylogenetic 'primitiveness' of *P. furiosus* in comparison to higher organisms whose carboxypeptidases have more specific purposes; for instance, human carboxypeptidase N deactivates bioactive peptides by hydrolyzing only basic C-terminal residues. Although ZAS, ZAH, and ZAN were hydrolyzed, the assay was not sensitive enough to detect hydrolysis under standard conditions; hence digestion times were increased to 30 minutes in order to detect activity. However, PfuCP activity at 80° C. in the presence of 0.4 mM $Co^{2+}$ with ZAR as substrate were determined from Lineweaver-Burke analysis: $K_m$, 2 mM; $V_{max}$, 2100 $U.mg^{-1}$; and turnover number, 2000 $s^{-1}$ (FIG. 9B).

Figure 10A:
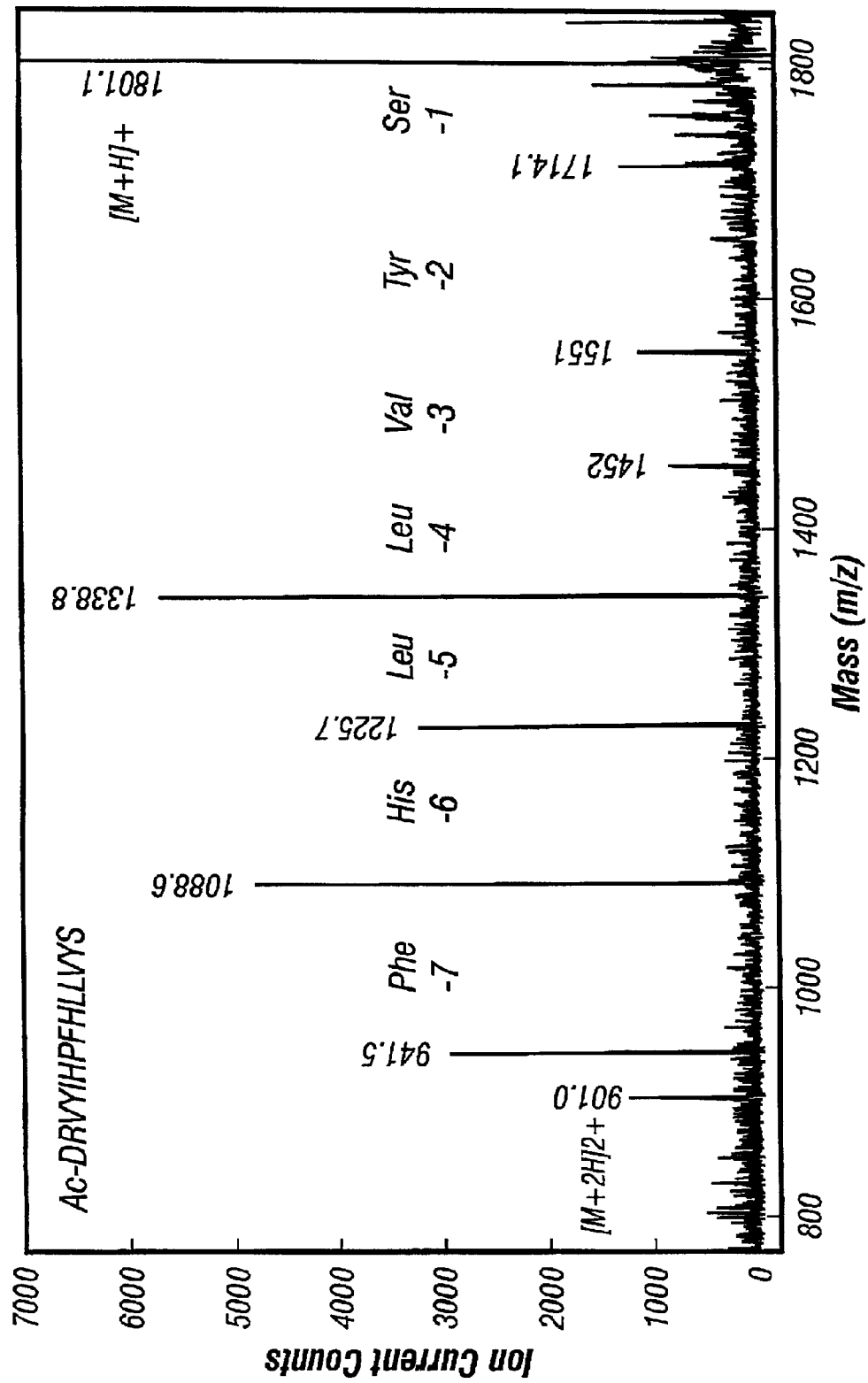
FIG. 10 shows the C-terminal ladder sequencing of N-acetyl-renin substrate by PfuCP. (A) The digestion was performed in 5 mM KMES buffer (pH 6.5) with 50 µM N-acetyl-renin substrate, 0.4 mM $CoCl_2$, and 150 nM purified apoPfuCP (total volume 5 µl). (B) The reaction was carried out for 1 minute at 80° C. followed by quenching on ice and the addition of 0.1% TFA. The sample was subsequently analyzed by MALDI-TOF MS and the monoisotopic masses were recorded.
Figure 10B:
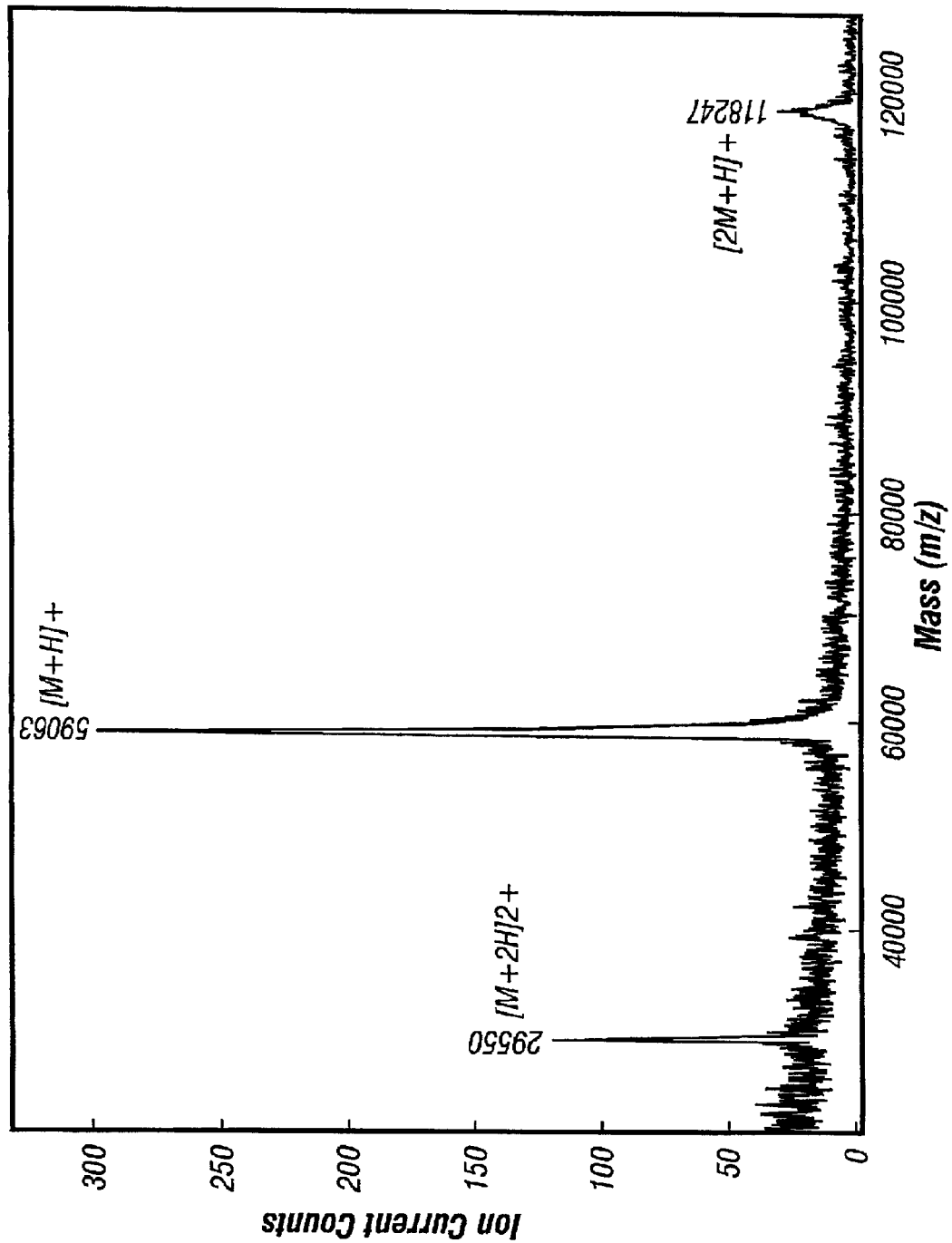

C-terminal Ladder Sequencing: Sequential C-terminal hydrolysis of the peptide N-acetylrenin substrate (NARS) by PfuCP, followed by MALDI-TOF MS detection, offered unambiguous proof of carboxypeptidase activity (FIG. 10). At 80° C., PfuCP was able to sequence up to 7 residues from the C-terminus of NARS releasing leucine, valine, phenylalanine, tyrosine, serine, and histidine residues. Sequencing of NARS at room temperature yields a similar mass spectrum, however, the intensity is greater for mass peaks that are closer to the C-terminus (right side of the mass spectrum), indicating a less complete digestion. Several other natural and synthetic peptides were also digested by PfuCP; digestion conditions are currently being optimized to show complete ladders. These sequencing experiments confirm the broad specificity of PfuCP demonstrated in the experiments with N-blocked ZAX dipeptides and represent the first reported instance of high-temperature C-terminal sequencing. Studies are underway to sequence larger proteins.

Summary: An inactive metallocarboxypeptidase (PfuCP) has been purified from the hyperthermophilic archaeon *P. furiosus* and its activity has been restored by the addition of $Co^{2+}$. Careful choice of substrate for the purification assay was necessary to ensure true carboxypeptidase activity, as many carboxypeptidase substrates are susceptible to hydrolysis by endoproteases or enzymes with mixed specificities. PfuCP has the highest optimal temperature of any carboxypeptidase purified to date; furthermore, its wide temperature range for activity (down to at least 20° C.) will conveniently allow many aspects of mechanism and thermoactivation to be examined.

The broad specificities of PfuCP against synthetic and natural peptide substrates suggest a role for PfuCP in digestion and protein turnover as opposed to specific post-translational modification seen in higher organisms. Further, the high temperature C-terminal enzymatic ladder sequencing reported here illustrates the inherent biotechnological potential of enzymes from hyperthermophiles.

---

What is claimed is:

1. A substantially purified polypeptide comprising any two or more of the following sequences:
   (a) SEQ ID No:1;
   (b) SEQ ID NO:2; and
   (c) SEQ ID NO:3, and
   wherein the polypeptide comprises:
   (a) a monomeric molecular weight of about 58 kDa by SDS-PAGE,
   (b) a monomeric molecular weight of about 59 kDa as determined by matrix-assisted laser desorption time-of-flight mass spectrometry, and
   (c) comprises carboxypeptidase activity in the presence of a divalent cation.

2. A substantially purified polypeptide of claim 1, wherein the polypeptide comprises a dimeric molecular weight of about 128 kDa by gel filtration chromatography.

3. The substantially purified polypeptide of claim 1, wherein the divalent cation is selected from the group consisting of $Co^{2+}$, $Ca^{2+}$, $Ni^{2+}$, $Fe^{2+}$, $Cd^{2+}$, $Cu^{2+}$, $Pb^{2+}$, $Rh^{2+}$, $Mn^{2+}$ and $Zn^{2+}$.

4. The substantially purified polypeptide of claim 1, wherein the polypeptide is obtained from *P. furiosus*.

5. A carboxypeptidase comprising an isolated homodimer of a polypeptide comprising any two or more of the following sequence SEQ ID NO:1, SEQ ID NO:2, or SEQ ID NO:3, and where the homodimer has a molecular weight of about 128 kDa by gel filtration chromatography.

6. The carboxypeptidase of claim 5, wherein the carboxypeptidase has a temperature optimum exceeding 90° C.

7. The carboxypeptidase of claim 5, wherein a monomeric form has a molecular weight of about 58 kDa by SDS-PAGE.

8. The carboxypeptidase of claim 5, wherein a monomeric form has a a molecular weight of about 59 kDa as determined by matrix-assisted laser desorption time-of-flight mass spectrometry.

* * * * *

SEQUENCE LISTING

<160> NUMBER OF SEQ ID NOS: 6

<210> SEQ ID NO 1
<211> LENGTH: 30
<212> TYPE: PRT
<213> ORGANISM: Pyrococcus furiosus

<400> SEQUENCE: 1

Met Glu Glu Val Phe Gln Asn Glu Thr Ile Lys Gln Ile Leu Ala Lys
 1               5                  10                  15

Tyr Arg Arg Ile Trp Ala Ile Gly His Ala Gln Arg Val Leu
            20                  25                  30

<210> SEQ ID NO 2
<211> LENGTH: 32
<212> TYPE: PRT
<213> ORGANISM: Pyrococcus furiosus

<400> SEQUENCE: 2

Glu Gly Ile Leu Glu Arg Ser Val Ala Gln Gly Glu Leu Ser Val Leu
 1               5                  10                  15

Ser His Glu Leu Leu Leu His Pro Glu Phe Val Asn Leu Val Glu Lys
            20                  25                  30

<210> SEQ ID NO 3
<211> LENGTH: 16
<212> TYPE: PRT
<213> ORGANISM: Pyrococcus furiosus

<400> SEQUENCE: 3

Ala Ile Gly Glu Asp Met Asp Ala Glu Tyr Phe Val Arg Trp Val Lys
 1               5                  10                  15

<210> SEQ ID NO 4
<211> LENGTH: 46
<212> TYPE: PRT
<213> ORGANISM: Pyrococcus horikoshii

<400> SEQUENCE: 4

Met Glu Thr Val Leu Arg Arg Leu His Leu Glu Lys Ser Gly Glu Thr
 1               5                  10                  15

Met Glu Glu Val Phe Arg Asn Asp Thr Ile Lys Glu Ile Leu Gln Lys
            20                  25                  30

Tyr Arg Arg Ile Trp Ala Leu Gly His Ala Gln Ser Val Leu
        35                  40                  45

```
-continued

<210> SEQ ID NO 5
<211> LENGTH: 32
<212> TYPE: PRT
<213> ORGANISM: Pyrococcus horikoshii

<400> SEQUENCE: 5

Glu Gly Ile Leu Glu Arg Ser Val Ala Gln Gly Glu Leu Ser Val Leu
 1               5                  10                  15

Ser Gln Glu Leu Leu Leu Lys Pro Glu Phe Val Glu Leu Val Glu Lys
            20                  25                  30

<210> SEQ ID NO 6
<211> LENGTH: 16
<212> TYPE: PRT
<213> ORGANISM: Pyrococcus horikoshii

<400> SEQUENCE: 6

Ala Ile Gly Glu Asp Val Asn Ala Glu Tyr Phe Val Arg Trp Ile Lys
 1               5                  10                  15
```